US010350312B2

(12) United States Patent
Zabow et al.

(10) Patent No.: US 10,350,312 B2
(45) Date of Patent: Jul. 16, 2019

(54) MAGNETIC MICROSTRUCTURES FOR MAGNETIC RESONANCE IMAGING

(71) Applicants: The United States of America, as Represented by the Secretary, Dept. of Health and Human Services, Washington, DC (US); THE UNITED STATES OF AMERICA, REPRESENTED BY THE SECRETARY OF COMMERCE, Washington, DC (US)

(72) Inventors: Gary Zabow, Boulder, CO (US); Stephen Dodd, Rockville, MD (US); Alan Koretsky, Bethesda, MD (US); John Moreland, Louisville, CO (US)

(73) Assignees: The United States of America, as Represented by the Secretary, Department of Health and Human Services, Washington, DC (US); The United States of America, as represented by the Sectretary of Commerce, Washington, DC (US)

( * ) Notice: Subject to any disclaimer, the term of this patent is extended or adjusted under 35 U.S.C. 154(b) by 0 days.

(21) Appl. No.: 14/738,296

(22) Filed: Jun. 12, 2015

(65) Prior Publication Data
US 2015/0367002 A1 Dec. 24, 2015

Related U.S. Application Data

(62) Division of application No. 12/937,843, filed as application No. PCT/US2009/041142 on Apr. 20, 2009, now Pat. No. 9,084,820.

(60) Provisional application No. 61/071,263, filed on Apr. 18, 2008.

(51) Int. Cl.
A61B 5/055 (2006.01)
A61K 49/18 (2006.01)
G01R 33/12 (2006.01)
G01R 33/28 (2006.01)
G01R 33/56 (2006.01)
G01R 33/563 (2006.01)
H01F 10/14 (2006.01)
G01R 33/34 (2006.01)

(52) U.S. Cl.
CPC .......... A61K 49/1818 (2013.01); A61B 5/055 (2013.01); A61K 49/18 (2013.01); A61K 49/1896 (2013.01); G01R 33/1269 (2013.01); G01R 33/281 (2013.01); G01R 33/5601 (2013.01); G01R 33/56366 (2013.01); H01F 10/14 (2013.01); G01R 33/34007 (2013.01); G01R 33/34084 (2013.01); G01R 33/5605 (2013.01); G01R 33/5607 (2013.01)

(58) Field of Classification Search
None
See application file for complete search history.

(56) References Cited

U.S. PATENT DOCUMENTS

| 5,342,608 A * | 8/1994 | Moriya ................ A61K 49/223 252/62.56 |
| 5,572,132 A | 11/1996 | Pulyer et al. |
| 6,377,048 B1 | 4/2002 | Golan et al. |
| 2003/0082237 A1* | 5/2003 | Cha .................. A61K 47/48861 424/490 |
| 2006/0099145 A1* | 5/2006 | Takeyama ............ A61K 9/1694 424/9.3 |
| 2006/0148104 A1* | 7/2006 | Marini ..................... B82Y 5/00 436/524 |
| 2007/0166730 A1 | 7/2007 | Menon et al. |

OTHER PUBLICATIONS

Yang et al. Preparation of poly epsilon-caprolactone nanoparticles containing magnetite for magnetic drug carrier. 2006 Int. J. Pharm. 324: 185-190.*
Viglianti et al. In vivo monitoring of tissue pharmacokinetics of liposome/drug using MRI: illustration of targeted delivery. 2004 Magn. Reson. Med. 51: 1153-1162.*
Xu et al. Generation of monodisperse particles by using microfluidics: control over size, shape, and composition. 2005 Angew. Chem. Int. Ed. Engl. 44: 724-728.*
Su et al. Nanoshell magnetic resonance imaging contrast agents. 2007 J. Am. Chem. Soc. 129: 2139-2146. Published online Jan. 31, 2007. (Year: 2007).*
Wang et al., Porous nanotubes of Co3O4: synthesis, characterization, and magnetic properties. 2004 Appl. Phys. Lett. 85:2080-2082.
Liu et al., Surfactant-assisted synthesis of alpha-Fe2O3 nanotubes and nanorods with shape-dependent magnetic properties. 2006 J. Phys. Chem. B 110: 15218-15223.

(Continued)

Primary Examiner — Michael G. Hartley
Assistant Examiner — Jennifer Lamberski
(74) Attorney, Agent, or Firm — Ron Galant; Polsinelli PC

(57) ABSTRACT

The present invention relates to magnetic contrast structures for magnetic resonance imaging, and methods of their use. The contrast structures include magnetic materials arranged as a pair of disk-shaped magnetic components with a space between a circular surface of each disk shape, or a tubular magnetic structure, a substantially cylindrical magnetic structure, a substantially spherical shell-formed magnetic structure, or a substantially ellipsoidal shell-formed structure, each defining a hollow region therein. The space and/or hollow region in the contrast structure creates a spatially extended region contained within a near-field region of the contrast structure over which an applied magnetic field results in a homogeneous field, such that nuclear magnetic moments of a second material when arranged within the spatially extended region precess at a characteristic Larmor frequency, whereby the contrast structure is adapted to emit a characteristic magnetic resonance signal of the magnetic material.

10 Claims, 26 Drawing Sheets

(56) References Cited

OTHER PUBLICATIONS

Bai et al, "Synthesis of Superparamagnetic Nanotubes as MRI Contrast Agents and for Cell Labeling", Nanomedicine, 2008, pp. 163-174, vol. 3, No. 2.

Lanza et al, "(1)H/(19)F Magnetic Resonance Molecular Imaging with Perfluorocarbon Nanoparticles", Current Topics in Developmental Biology, 2005, pp. 57-76; vol. 70, No. 1.

Seevinck et al, "Factors Affecting the Sensitivity and Detection Limits of MRI, CT, and SPECT for Multimodal Diagnostic and Therapeutic Agents", Anti-Cancer Agents in Medicinal Chemistry, 2007, pp. 317-334, vol. 7, No. 3.

Sitharaman et al, "Superparamagnetic Gadonanotubes are High-Performance MRI Contrast Agents", Chem. Commu., 2005, pp. 3915-3917, No. 31.

Sukstanskii et al, "Theory of FID NMR Signal Dephasing Induced by Mesocopic Magnetic Field Inhomogeneities in Biological Systems", Journal of Magnetic Resonance, 2001, pp. 107-117, vol. 151, No. 1.

Woods et al, "Paramagnetic Lanthanide Complexes as Paracest Agents for Medical Imaging", Chemical Society Reviews, 2006, pp. 500-511, vol. 35, No. 6.

Zabow et al, "Design and Fabrication of a Micromachined Multispectral Magnetic Resonance Imaging Agent", J. Micromech. Microeng., 2009, pp. 1-10, vol. 19, No. 2.

Zabow et al., "Micro-Engineered Local Field Control for High-Sensitivity Multispectral MRI", Nature, 2008, pp. 1058-1063, vol. 453, No. 7198.

\* cited by examiner

MAGNETIC MICROSTRUCTURES FOR MAGNETIC RESONANCE IMAGING

CROSS-REFERENCE TO RELATED APPLICATION

This application claims priority to U.S. Provisional Application No. 61/071,263 filed Apr. 18, 2008, the entire contents of which are hereby incorporated by reference.

BACKGROUND

1. Field of Invention

The present invention relates to magnetic resonance identity systems, magnetic resonance imaging contrast agents and spectroscopic agents, and magnetic microstructures for magnetic resonance systems and methods of production.

2. Discussion of Related Art

Magnetic resonance imaging (Lauterbur, P. C. Image formation by induced local interactions: examples employing nuclear magnetic resonance. *Nature* 242, 190-191 (1973); Mansfield, P. & Grannell P. K. NMR 'diffraction' in solids? *J. Phys. C* 6, L422-L426 (1973)) (MRI) has become an invaluable, widely used medical diagnostic and research tool (Callaghan, P. T. *Principles of nuclear magnetic resonance microscopy*. (Oxford Univ. Press, New York, 1991)). Nevertheless, despite numerous chemically-synthesized image-enhancing agents (Nelson, K. L. & Runge, V. M. Basic principles of MR contrast. *Topics in Magn. Reson. Imaging* 7, 124-136 (1995); Runge, V. M. & Wells, J. W. Update: safety, new applications, new MR agents. *Topics in Magn. Reson. Imaging* 7, 181-195 (1995); Weissleder, R. et al. Ultrasmall superparamagnetic iron oxide: characterization of a new class of contrast agents for MR imaging. *Radiology* 175, 489-493 (1990); Woods, M., Woessner, D. E. & Sherry, A. D. Paramagnetic lanthanide complexes as PARACEST agents for medical imaging. *Chem. Soc. Rev.* 35, 500-511 (2006); Lanza, G. M. et al. $^1H/^{19}F$ magnetic resonance molecular imaging with perfluorocarbon nanoparticles. *Current Topics in Devel. Bio.* 70, 57-76 (2005)), MRI still lacks the sensitivity and the multiplexing capabilities of optical imaging that benefits from colored fluorophores (Mason, W. T. (ed) *Fluorescent and Luminescent Probes for Biological Activity*. (Academic Press, London, 1999)), multi-spectral quantum dots (Bruchez, M. Jr., Moronne, M., Gin, P., Weiss, S. & Alivisatos, A. P. Semiconductor nanocrystals as fluorescent biological labels. *Science* 281, 2013-2016 (1998); Chan, W. C. W. & Nie, S. Quantum dot bioconjugates for ultrasensitive nonisotopic detection. *Science* 281, 2016-2018 (1998); Alivisatos, P. The use of nanocrystals in biological detection. *Nat. Biotechnol.* 22, 47-52 (2004)), and microfabricated barcodes (Nicewarner-Peña, S. R. et al. Submicrometer metallic barcodes. *Science* 294, 137-141 (2001)), for multi-functional encoding and biomolecular/cellular labeling.

Being able to distinguish with MRI between different types of cells, at the single cell level, would profoundly impact cellular biology and early disease detection and diagnosis. Currently, MRI cell tracking employs the magnetically dephased signal from the water surrounding cells labeled with many superparamagnetic iron oxide nanoparticles (Weissleder, R. et al. Ultrasmall superparamagnetic iron oxide: characterization of a new class of contrast agents for MR imaging. *Radiology* 175, 489-493 (1990); Dodd, S. J. et al. Detection of single mammalian cells by high-resolution magnetic resonance imaging. *Biophys. J.* 76, 103-109 (1999); Cunningham, C. H. et al. Positive contrast magnetic resonance imaging of cells labeled with magnetic nanoparticles. *Magn. Reson. Med.* 53, 999-1005 (2005)) (SPIOs) or dendrimers (Bulte, J. W. M. et al. Magnetodendrimers allow endosomal magnetic labeling and in vivo tracking of stem cells. *Nat. Biotechnol.* 19, 1141-1147 (2001)), or individual micrometer-sized iron oxide particles (Hinds, K. A. et al. Highly efficient endosomal labeling of progenitor and stem cells with large magnetic particles allows magnetic resonance imaging of single cells. *Blood.* 102, 867-872 (2003); Shapiro, E. M., Skrtic, S. & Koretsky, A. P. Sizing it up: cellular MRI using micron-sized iron oxide particles. *Magn. Reson. Med.* 53, 329-338 (2005)) (MPIOs) that benefit from increased robustness and immunity to label dilution via cell division. However, the continuous spatial decay of the external fields surrounding these, or any other, magnetizable particles imposes a continuous range of Larmor frequencies that broadens the water line, obscuring distinction between possible different types of magnetic particles that might specifically label different types of cells. Their utility would be greatly enhanced if they could instead frequency shift the water by discrete controllable amounts, transforming a monochrome/binary contrasting agent (magnetically labeled or not) into a "colored" spectral set of distinguishable tags. There is thus a need for improved magnetic resonance imaging contrast agents.

SUMMARY

A magnetic resonance contrast agent according to an embodiment of the current invention has a medium, and a contrast structure dispersed in the medium. The contrast structure comprises a magnetic material arranged to create a local region of a local magnetic field such that nuclear magnetic moments of a material when arranged within said local region precess at a characteristic Larmor frequency about a total magnetic field in the local region while in use, the characteristic Larmor frequency being identifiable with the contrast structure, and the total magnetic field in the local region being a substantially spatially uniform magnetic field.

A magnetic resonance structure for use with a magnetic resonance system has a magnetic material arranged in a configuration so as to create a local region of a local magnetic field such that nuclear magnetic moments of a material when arranged within the local region precess at a characteristic Larmor frequency about a total magnetic field in the local region while in use, the characteristic Larmor frequency being identifiable with the magnetic resonance structure, and the total magnetic field in the local region being a substantially spatially uniform magnetic field.

A magnetic resonance identity system has a magnetic resonance structure, a source of electromagnetic radiation arranged to illuminate the magnetic resonance structure with excitation radiation; and a detection system constructed and arranged to detect characteristic magnetic resonance signals emitted from the magnetic resonance structure. The magnetic resonance structure comprises a magnetic material arranged to create a local region of a local magnetic field such that nuclear magnetic moments of a material when arranged within the local region precess at a characteristic Larmor frequency about a total magnetic field in the local region while in use, the characteristic Larmor frequency being identifiable with the magnetic resonance structure, and the total magnetic field in the local region being a substantially spatially uniform magnetic field.

A method of producing a magnetic resonance contrast agent includes forming a plurality of contrast structures on a substrate, separating the plurality of contrast structures from the substrate, and dispersing the plurality of contrast structures in a medium. The contrast structure comprises a magnetic material arranged to create a local region of a local magnetic field such that nuclear magnetic moments of a material when arranged within the local region precess at a characteristic Larmor frequency about a total magnetic field in the local region while in use, the characteristic Larmor frequency being identifiable with the contrast structure, and the total magnetic field in the local region being a substantially spatially uniform magnetic field.

BRIEF DESCRIPTION OF THE DRAWINGS

Additional features of this invention are provided in the following detailed description of various embodiments of the invention with reference to the drawings. Furthermore, the above-discussed and other attendant advantages of the present invention will become better understood by reference to the detailed description when taken in conjunction with the accompanying drawings, in which.

particles and a background-subtracted MRI showing transferred magnetization saturation from the particles' shifted resonance. A scratch (lower right) removed about one hundred particles (about 10-20 per voxel). Its visibility in the MR image suggests the potential for high-resolution imaging to spectrally distinguish individual such particles.

Figure 18A:
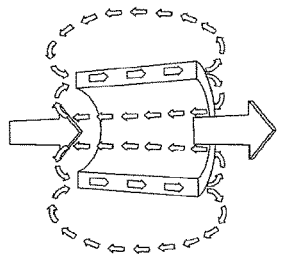
Figure 18B:
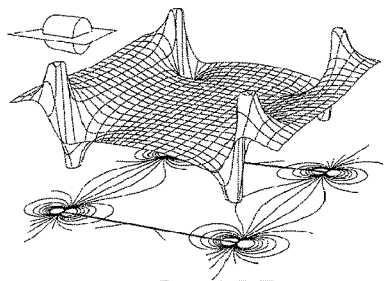
Figure 18C:
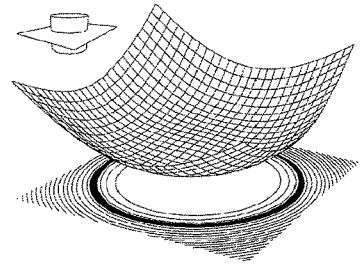
Figure 18D:
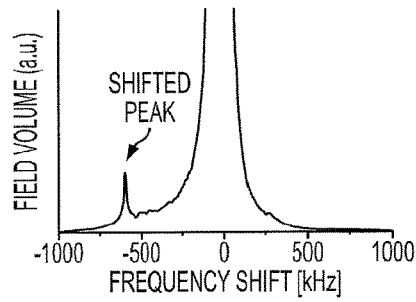
Figure 18E:
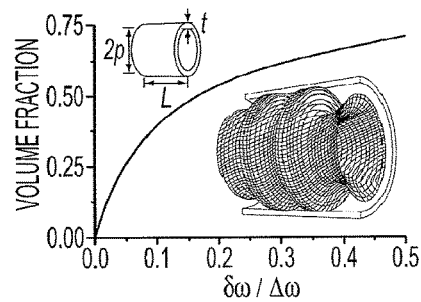

FIGS. 18A-18E provide a schematic illustration of a magnetic resonance structure according to another embodiment of the current invention. FIG. 18A shows a cut-away schematic illustration of the field (small arrows) of a hollow cylinder magnetized to saturation by background MRI field $B_0$ (large arrows). FIG. 18B shows the calculated magnetic field magnitude profile with underlying field magnitude contour plot in a mid-plane through a magnetized hollow cylinder (plane orientation shown in upper left corner). FIG. 18C corresponds to FIG. 18B but for perpendicularly oriented mid-plane. FIG. 18D shows a histogram recording the frequency shifts that would be experienced by the water surrounding the hollow cylinder (see text). FIG. 18E shows calculated cylindrical shell internal volume fraction falling within a bandwidth $\delta\omega$, about the shell's central frequency shift $\Delta\omega$. The inset cut-away schematic shows the characteristic spatial extent of the hollow cylinder's internal homogeneous field volume for a cylinder aspect ratio $L/2\rho=1.2$: all points within the numerically calculated 3-dimensional hatched surface contour, have frequency shifts differing from $\Delta\omega$ by no more than ±5%.

Figure 19A:
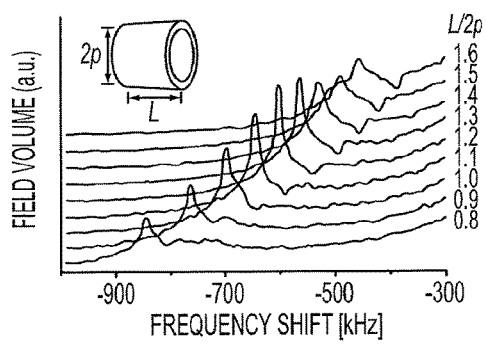
Figure 19B:
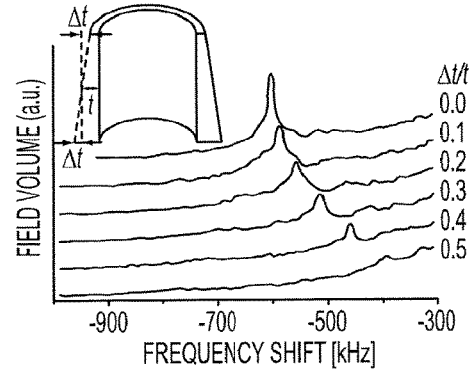

FIGS. 19A-19B show spectral linewidth dependence on cylinder geometry according to an embodiment of the current invention. FIG. 19A shows a vertically-offset waterfall-style plot of calculated frequency histograms for thin-walled cylinders (t<<L), showing optimal aspect ratio, $L/2\rho\approx1.2$. FIG. 19B shows a vertically-offset waterfall-style plot of calculated frequency histograms for cylinders with non-uniform wall thickness. Labels indicate ratio of thickness change $\Delta t$, to average thickness t.

Figure 20A:
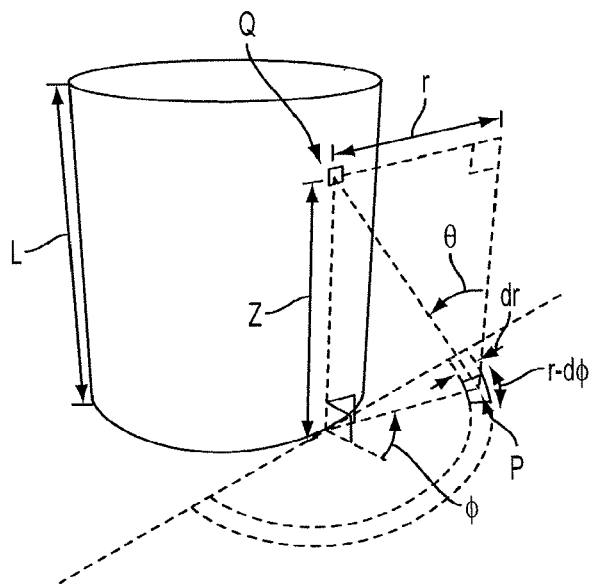
Figure 20B:
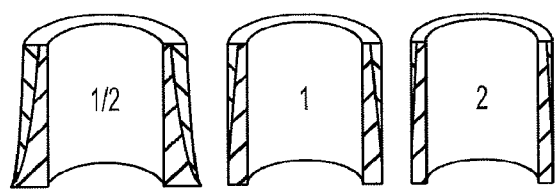

FIGS. 20A-20B illustrate local sidewall sputter coating according to embodiment of the current invention. FIG. 20A provides a schematic illustration of geometry used in sputtering calculation (see text). FIG. 20B shows calculated sidewall coating thicknesses for $\cos^{1/2}\theta$, $\cos\theta$, and $\cos^2\theta$ sputter distributions and associated calculated sidewall sputter-coating thicknesses (labels indicate cosine powers). Dark grey indicates sidewall thickness profile for R/L=2 (see text); light and dark grey together indicate overall profile for R/L=10.

Figure 21A:
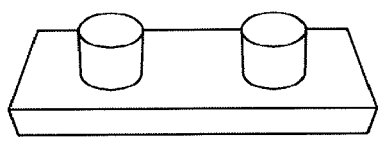
Figure 21D:
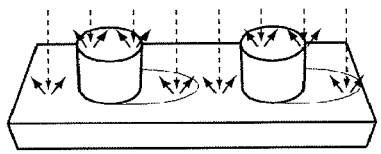
Figure 21B:
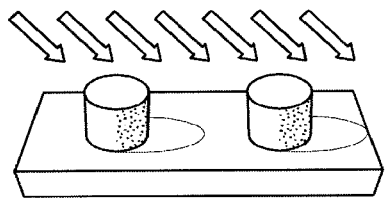
Figure 21E:
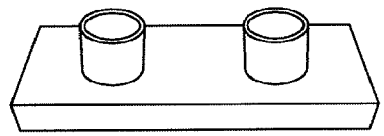
Figure 21C:
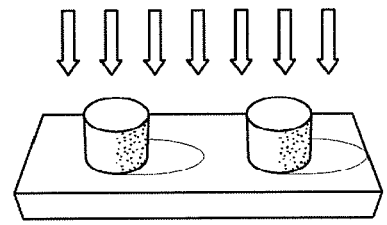
Figure 21F:
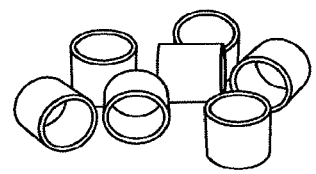

FIGS. 21A-21F provide a process flow diagram for cylindrical nanoshell fabrication according to an embodiment of the current invention. FIG. 21A shows patterned cylindrical photoresist posts atop a gold-titanium coated substrate, FIG. 21B shows angled copper evaporation, FIG. 21C shows magnetic material evaporation, FIG. 21D shows ion-milling removal of magnetic material and local resputtered coating of posts, FIG. 21E shows copper and photoresist removal, and FIG. 21F shows release of hollow cylinders by gold-etch or ultrasound.

Figure 22A:
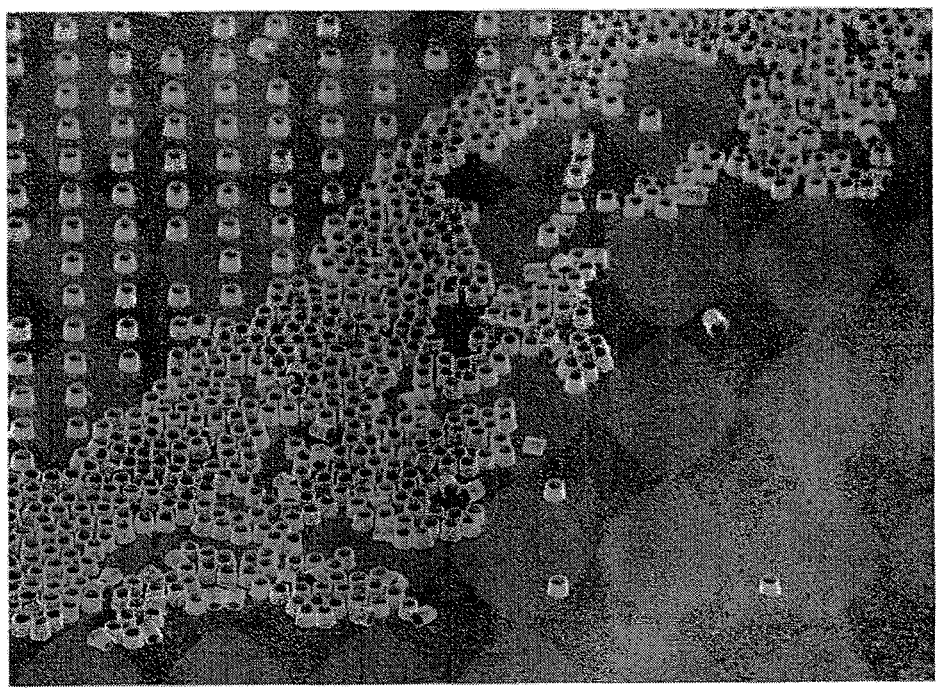
Figure 22B:
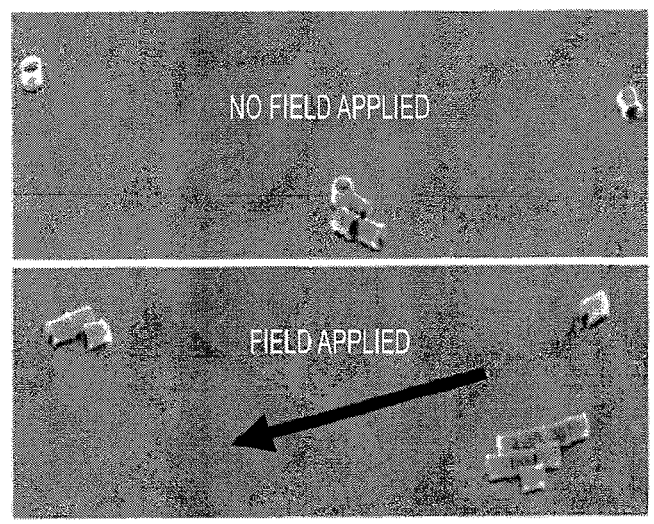

FIGS. 22A-22B show scanning electron micrographs (SEM) of fabricated cylindrical nanoshells according to an embodiment of the current invention. FIG. 22A is an SEM showing partial wet-etch release of an array of cylindrical nanoshells ($\rho\approx1$ µm, shell thickness t$\approx$75 nm) from a substrate. FIG. 22B provides SEM's of cylindrical nanoshells ($\rho\approx425$ nm, shell thickness t$\approx$40 nm) that were ultrasounded off their substrate and subsequently pipetted out onto fresh substrates according to an embodiment of the current invention. The top image in FIG. 22B shows nanoshells pipetted out in the absence of any applied magnetic field. The bottom image shows the same process but with background magnetic field applied illustrating automatic self-alignment of the cylindrical nanoshells with the applied field direction (black arrow).

Figure 23A:
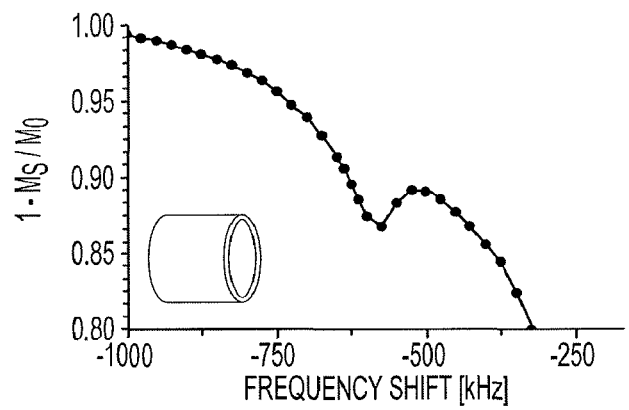
Figure 23B:
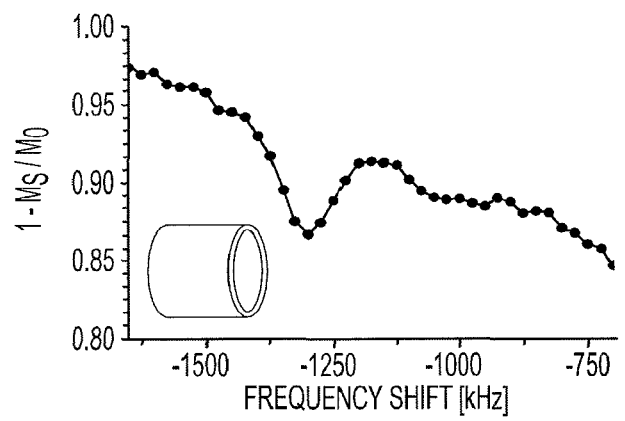
Figure 23C:
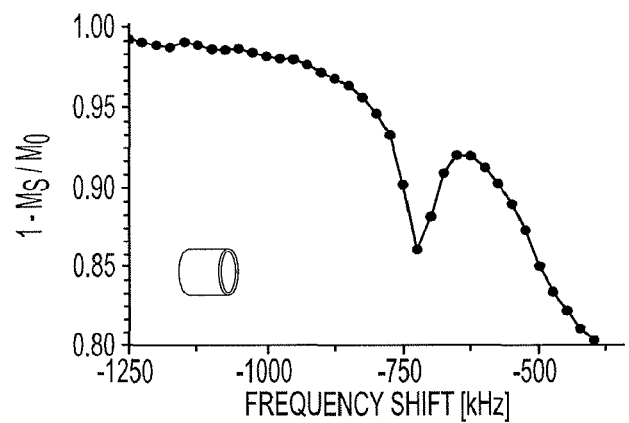
Figure 23D:
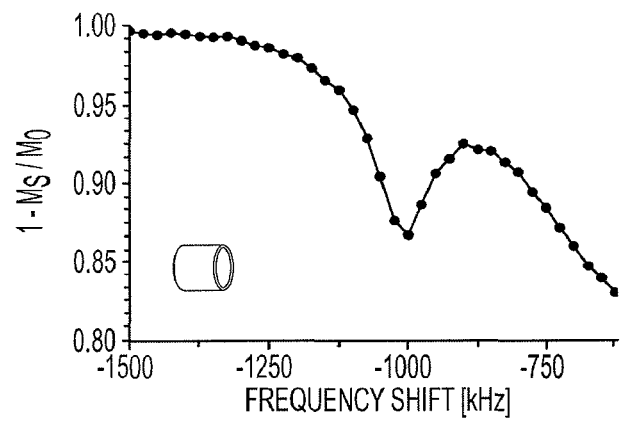
Figure 23E:
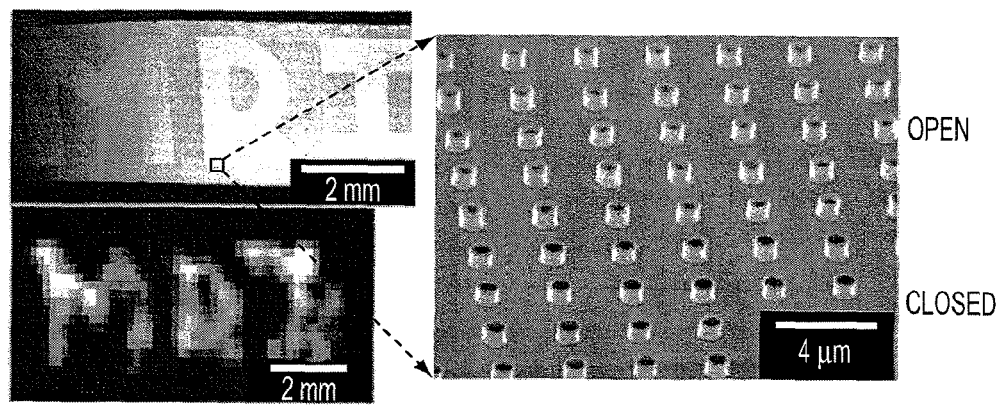

FIGS. 23A-23E show spectral contrast for $H_2O$ z-spectra showing frequency-dependent fractional proton magnetization saturation $M_z/M_0$, from water-submerged cylindrical nanoshells according to an embodiment of the current invention with radii $\rho$, and shell thicknesses t, of: FIG. 23A) $\rho\approx1$ µm, t$\approx$75 nm; FIG. 23B) $\rho\approx1$ µm, t$\approx$150 nm; FIG. 23C) $\rho\approx425$ nm; t$\approx$40 nm; FIG. 23D) $\Sigma\approx450$ nm; t$\approx$50 nm. All cylinder aspect ratios are $L/2\rho\approx1.2$. FIG. 23E shows low and high magnification SEM's of array of cylindrical nanoshells ($\rho\approx450$ nm; t$\approx$60 nm) with all shell interiors, except for those comprising the "MRI" lettering, blocked to "turn off" their spectrally-shifted signals. Also shown is an MRI (bottom left) of the array formed from the difference between two images: one collected after first saturating out proton magnetization around 1.25 MHz (corresponding to the measured nanoshell resonance); the other a background image acquired without any proton magnetization saturated out. Signal is visible only from those shells with open interiors that allow water to diffuse in and out.

Figure 24:
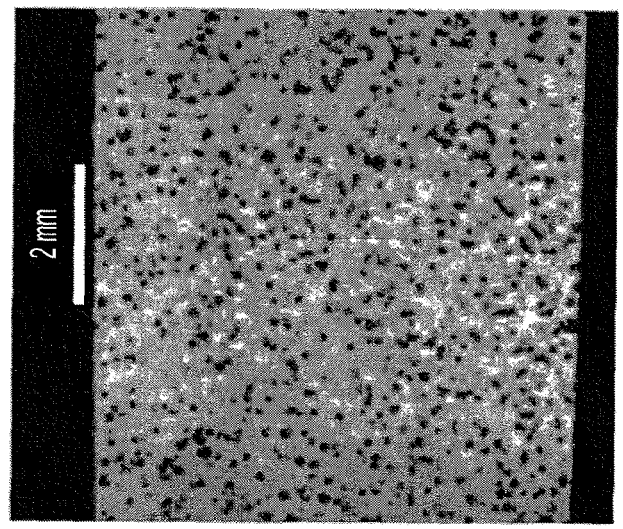

FIG. 24 shows gradient-echo MRI (50 µm isotropic resolution) showing hypointense $T_2^*$ contrast (dark spots) surrounding locations of cylindrical nanoshells suspended in agarose imaging phantom according top an embodiment of the current invention.

Figure 25:
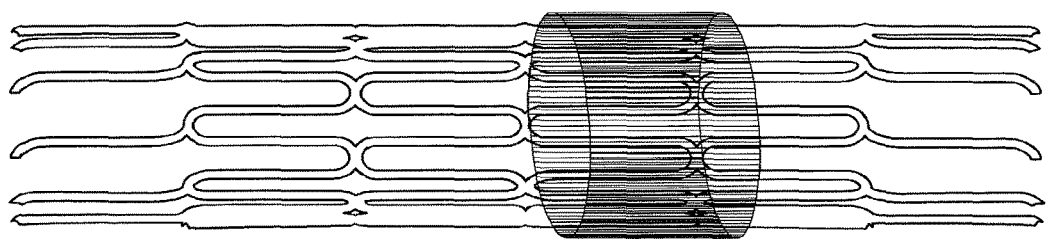

FIG. 25 is a schematic illustration of a magnetic resonance structure according to another embodiment of the current invention.

Figure 26:
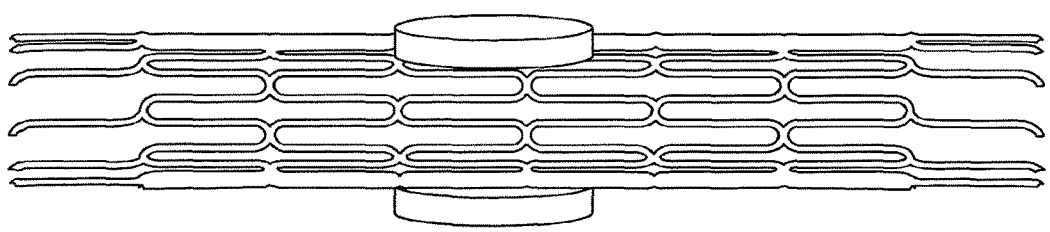

FIG. 26 is a schematic illustration of a magnetic resonance structure according to another embodiment of the current invention.

Figure 27:
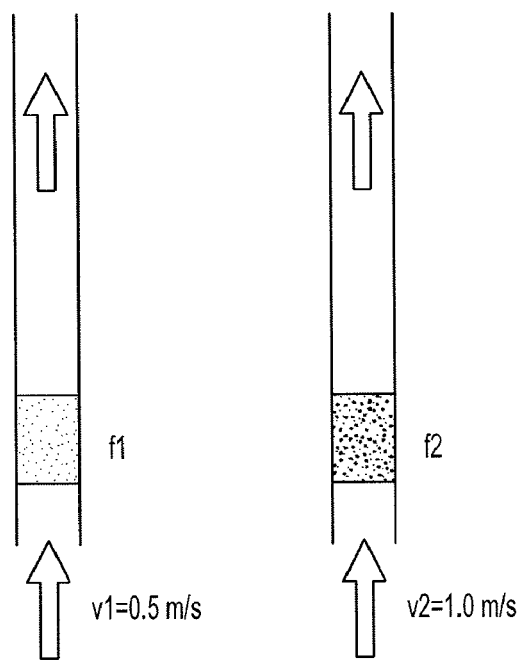

FIG. 27 is a schematic illustration to help describe the concept of flow 'tagging' with a large cylindrical version of a magnetic resonance structure according to an embodiment of the current invention.

Figure 28:
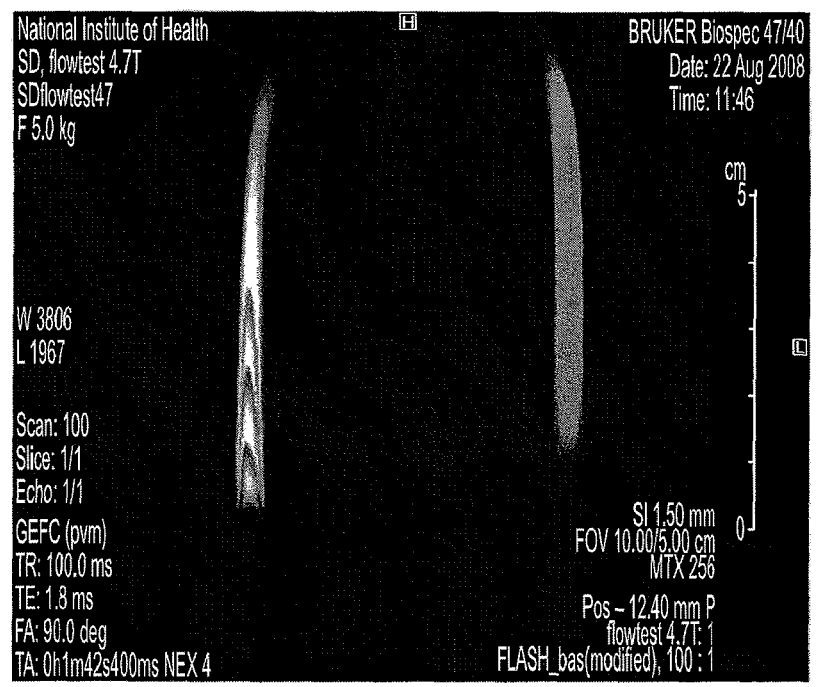

FIG. 28 shows experimental results for an embodiment corresponding to FIG. 27, where the left tube has slower velocity. The characteristic parabolic laminar flow profile is shown in the three tags.

Figure 29:

FIG. 29 shows experimental results for an embodiment corresponding to FIG. 27, which has faster velocity than FIG. 28, but similar results.

Figure 30:

FIG. 30 shows experimental results for an embodiment corresponding to FIG. 27 for perfusion imaging where the RF labeling pulses are spaced close enough in time so as to appear continuous for the left tube.

Figure 31:
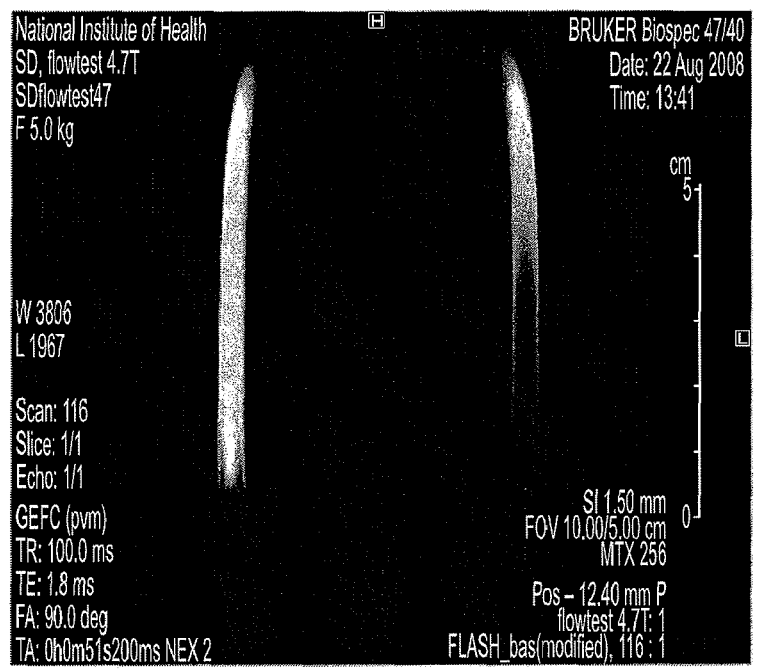

FIG. 31 shows experimental results similar to FIG. 30, but for the right tube.

DETAILED DESCRIPTION

All references cited anywhere in this specification are hereby incorporated by reference.

According to some embodiments of the current invention, we consider the advantages of top-down microfabrication for designing magnetic resonance agents with more directly engineered properties and increased functionality. The term microfabricated is intended to be broad and to refer generally to structures that are produced on a substrate. Typically, the structures will be produced by spatial patterning of a layer or layers of material on the substrate, such as, but not limited to, using lithographic techniques. Photolithographic techniques are intended to be included within the definition of microfabrication. Other lithographic techniques such as electron beam and other charge particle beam lithography, deep- and extreme-UV lithography, x-ray lithography, as well as micro and nano imprinting techniques are intended to be included within the definition of microfabrication. However, the term microfabricated is not intended to be limited to only these examples and is intended to cover all fabrication techniques generally referred to as top-down fabrication techniques. The term microfabrication is also intended to include the fabrication of structures that are as large as about 1 mm and as small as about 1 nm. Although the term microfabrication is used frequently throughout this specification and in the claims, it is intended to include nanofabrication. Chemical synthesis techniques that do not include at least one spatial patterning step, sometimes referred to as bottom-up synthesis, are not traditionally included within the definition of topdown microfabrication. However within certain possible alternative embodiments of the invention it may also be possible to chemically synthesize the necessary structures, provided that the chemical synthesis method can achieve sufficiently high levels of accuracy in fabricated structure geometry and inter-structure monodispersity. Possible chemical synthesis approaches are discussed later.

In some examples, we demonstrate a new imaging modality based on magnetic geometry rather than chemical structure, enabling multiplexed color MRI through what can be effectively sub-cellular-sized radio-frequency identification (RFID) tags. Engineered to exploit diffusion in some embodiments, these microstructures increase traditional MRI sensitivity by orders of magnitude, reducing required concentrations to well below those of existing contrast agents and potentially enabling individually detectable, spectrally distinct micro-tags. With signal frequencies determined by structural shape and composition instead of by chemical (Woods, M., Woessner, D. E. & Sherry, A. D. Paramagnetic lanthanide complexes as PARACEST agents for medical imaging. *Chem. Soc. Rev.* 35, 500-511 (2006)) or nuclear (Lanza, G. M. et al. $^1$H/$^{19}$F magnetic resonance molecular imaging with perfluorocarbon nanoparticles. *Current Topics in Devel. Bio.* 70, 57-76 (2005)) shift, spectral signatures can be arbitrarily tailored over uniquely broad shift ranges spanning many tens of thousands of parts per million. Beyond their RF analogy to continuously-tunable optical quantum dots, such microstructures may also enable a variety of localized physiological probes, enhancing both MRI capabilities and basic biological research. However, the general concepts of the current invention are not limited to only MRI contrast agents. Micro-tags according to other embodiments of the current invention may have a wide range of applications in analogy to the wide range of applications possible for quantum dots and/or RFID tags.

Spectral shifting by magnetic structures is possible by noting that even though all magnetic objects have continuous external field decays, this does not preclude frequency shifting nuclei contained within local regions of a structure's near-field zone such as, for example, internally either within a magnetizable shell or between neighbouring magnetizable elements. A distinct, resolvable frequency-shifted peak requires a spatially extended volume over which the additional field generated by the magnetizable structure results in a homogeneous field, either on its own, or in combination with a background magnetic field, that is preferably offset in magnitude from that of the structure's surrounding external decaying fields.

Figure 1:
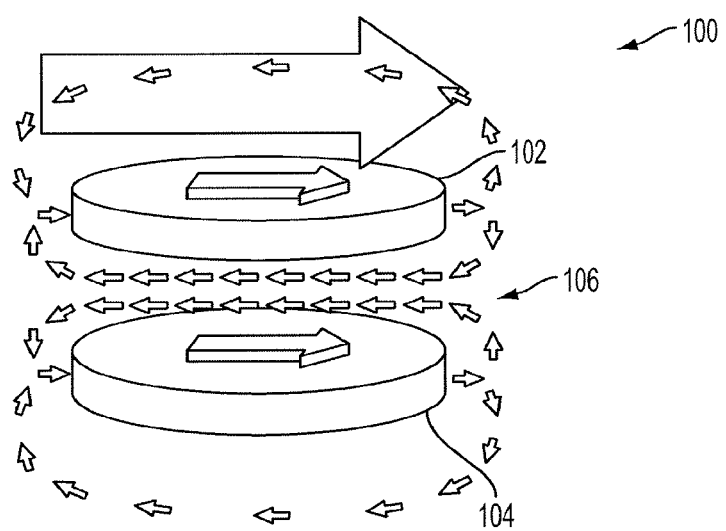
FIG. 1 is a schematic illustration of a magnetic resonance structure according to an embodiment of the current invention. The magnetic field (small arrows) from two parallel discs (an example of first and second magnetic portions) are magnetized to saturation by $B_0$ (large arrow). Non-magnetic spacer elements are not shown in this illustration.

FIG. 1 is a schematic illustration of a magnetic resonance structure 100 according to an embodiment of the current invention. The magnetic resonance structure 100 can be a magnetic resonance microstructure 100 in some embodiments of the current invention. In one embodiment according to the current invention, the magnetic resonance structure has two magnetic materials with a fixed space between them that can be filled with a non-magnetic liquid, paste or gas in some embodiments. In another embodiment, the magnetic resonance structure has an open ended cylindrical magnetic structure with a space within it that can be filled by a non-magnetic liquid, paste or gas. In another embodiment, the magnetic resonance structure is a substantially spherical or elliptical shell that can be filled with a non-magnetic liquid, paste or gas in some embodiments. The magnetic resonance structures can be magnetic resonance structures that are dispersed in a medium for use as a magnetic resonance contrast agent in some embodiments of the current invention. However, the general concepts of the current invention are not limited to only these particular embodiments.

Figure 6:
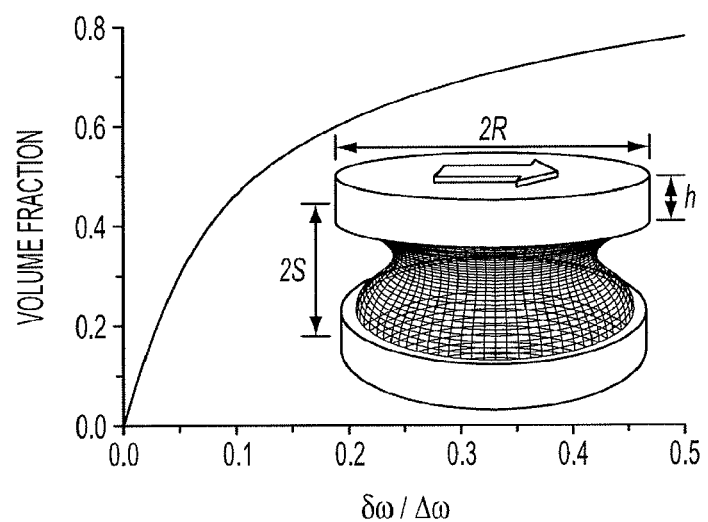
FIG. 6 shows calculated particle volume fraction that falls within a bandwidth, $\delta\omega$, about the particle's frequency shift, $\Delta\omega$, for a magnetic resonance microstructure according to an embodiment of the current invention. A sample numerical surface contour delineates the characteristic extent of this homogeneously shifted field region; all points inside the hatched contour shell have shifts within $\Delta\omega \pm \Delta\omega/50$.
Figure 7:
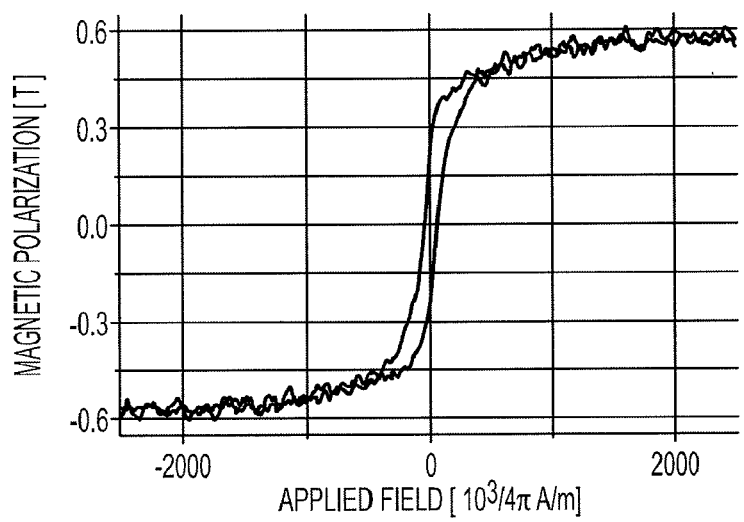
FIG. 7 shows an alternating-gradient magnetometer hysteresis curve of R=2.5 μm particles (magnetic resonance microstructures) according to an embodiment of the current invention that are shown in FIG. 9. The particles' nickel discs are fully saturated by applied fields well below standard MRI fields.
Figure 8:
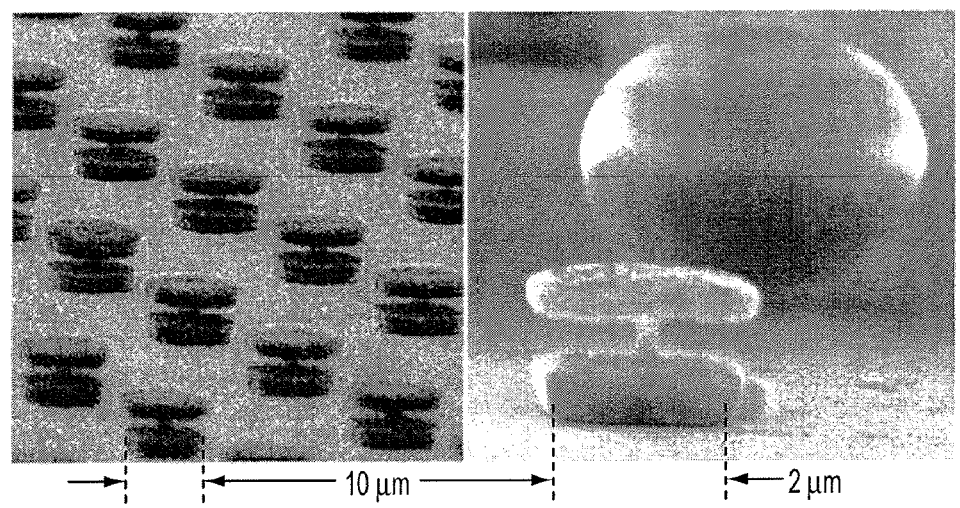
FIG. 8 shows scanning electron micrographs (SEM) of R≈5 μm, and R≈1 μm, microfabricated double-disc magnetic structures with non-magnetic internal supports according to an embodiment of the current invention. For relative size, a regular commercial 4.5 μm diameter MPIO (as commonly used for cell labeling/magnetic separation) is shown in the background.
Figure 9:
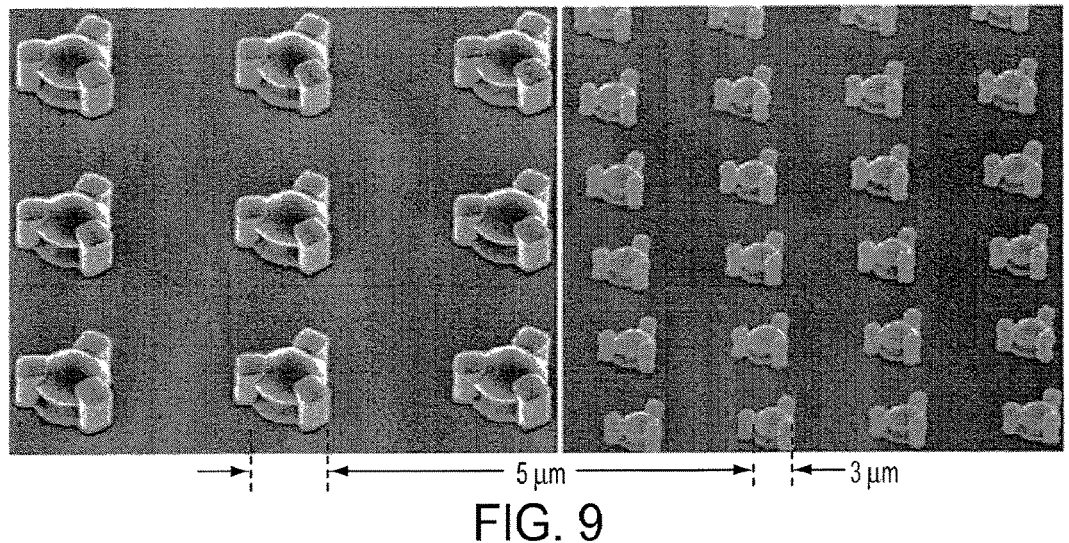
FIG. 9 shows SEM of externally-supported R=2.5 μm and 1.5 μm double-disc structures according to an embodiment of the current invention. In contrast to the examples of FIG. 8, these particles demonstrate relatively thin magnetic layers, h=50 nm, spaced 2S=2 μm (left side) and 1 μm (right side) apart. (The top surface's dome-like appearance is due to a non-magnetic capping layer used during microfabrication). These structures are robust, showing no discernible physical or magnetic change after month-long storage periods (both in and out of water).
Figure 10:
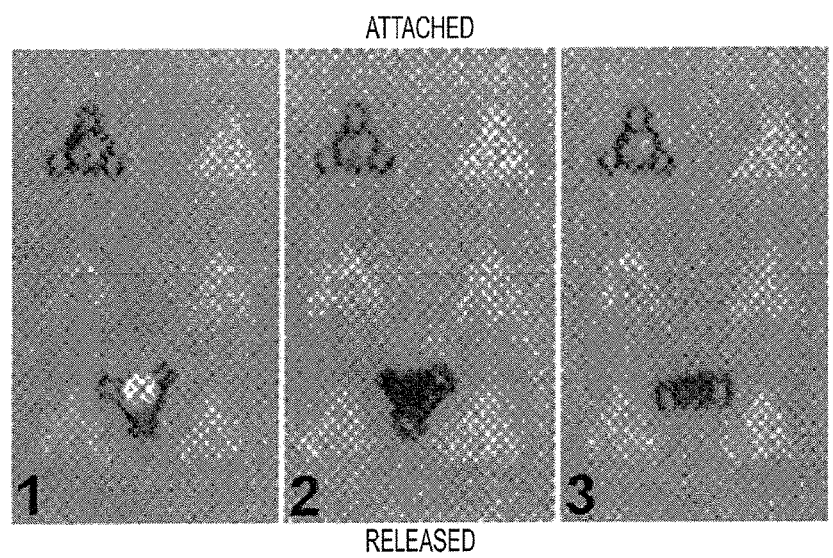
FIG. 10 shows a particle (an example of a magnetic resonance microstructure according to an embodiment of the current invention) still attached to the substrate, an R=5 μm particle released into water automatically self-aligns with an applied magnetic field that is rotated from in-plane to out-of-plane in the sequence (1),(2),(3).

The magnetic resonance structure 100 can be a magnetic resonance contrast structure for use with a magnetic resonance system according to an embodiment of the current invention. The magnetic resonance structure 100 has a magnetic material arranged in a configuration so as to create a local region of a local magnetic field such that nuclear magnetic moments of a material when arranged within the local region precess at a characteristic Larmor frequency about a total magnetic field in the local region while in use. The characteristic Larmor frequency is identifiable with the magnetic resonance structure 100 and the total magnetic field in the local region is a substantially spatially uniform magnetic field. The total magnetic field in the local region of the magnetic resonance structure 100 can be equal to the local magnetic field created by the magnetic resonance structure 100 in a case in which it is not embedded in an external magnetic field while in use, for example. In other embodiments, the total magnetic field in the local region of the magnetic resonance structure 100 can be a combination of the local magnetic field created by the magnetic resonance structure 100 and a portion of a background magnetic field when the magnetic resonance structure 100 is embedded in the background field during use. However, the general concepts of the current invention are not limited to only these examples. Note that by the term "local" we intend to imply a spatially extended region that is contained within the physical near-field region of the structure, as opposed to its far-field. The size of this near-field region scales with the size of the structure and is a region substantially centered on the structure and extending out from the structure to a distance of no more than a few times the maximum spatial dimension of the structure itself. The local region of interest within this near-field region is that region over which the total magnetic field is substantially uniform and substantially different in magnitude from any applied background magnetic field. Examples of such a "local" region include the central portion of the region between the two spaced magnetic disks, whose characteristic extent is indicated schematically by the green region in FIG. 6, or a portion of the region within a hollow cylinder, whose characteristic extent is indicated schematically by the yellow region in FIG. 18e.

Figure 2:
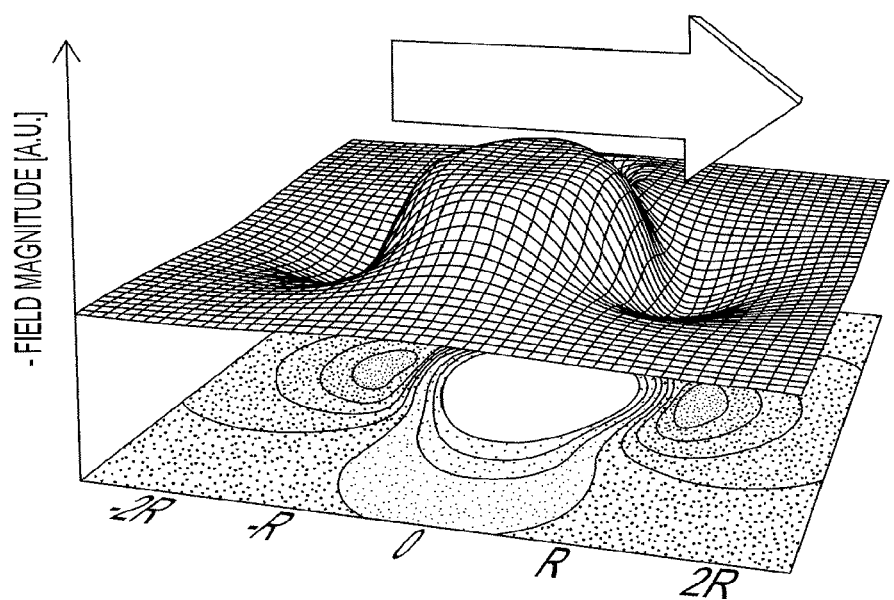
FIG. 2 shows the calculated (negative) field magnitude in the mid-plane through a typical magnetized disc set illustrated in FIG. 1 contrasting its homogeneous nature between the discs with its rapid external decay.

FIG. 2 shows a calculated magnetic field corresponding to the embodiment of FIG. 1. In some embodiments, the magnetic resonance structure 100 can be a micro-tag for example that could be attached to and/or incorporated within a biological cell, or that could be affixed to some other object to function in a manner similar to regular RFID labels (although here the tags are probed via a magnetic resonance). The magnetic resonance microstructure 100 has a first magnetic portion 102 and a second magnetic portion 104 arranged proximate the first magnetic portion 102 with a space 106 reserved therebetween. The local region of the local magnetic field is within the space 106 in this embodiment. The space 106 is suitable to accommodate a nonmagnetic material therein. The space 106 can permit a fluid to flow and/or diffuse through at least a portion of the local region of the local magnetic field in some embodiments.

The first 102 and second 104 magnetic portions are oriented with respect to each other to provide a region of substantially uniform magnetic field in the reserved space 106. The substantially uniform magnetic field is suitable for nuclear magnetic moments of the nonmagnetic material to be oriented therein in a high energy orientation and in a low energy orientation. When we refer to the substantially uniform/homogeneous field of the microstructures, there are two possible situations: i) when the object is being magnetized by a background MRI field that is much larger in magnitude than the fields generated by the microstructure, and ii) when the object is a permanent magnet and there is no background field or only a weak background field. In case i), because of the quadrature vector addition of fields, it is really only the component of the microstructures' fields that is parallel/antiparallel to the background MRI field that needs to be substantially uniform/homogeneous. In case ii), when the object is a permanent magnet and there is no background field or only a weak background field, the structure's entire field (ie every vector component) needs to be substantially uniform/homogeneous.

At least one of a material of the first 102 and second 104 magnetic portions, a dimension of the first 102 and second 104 magnetic portions or a distance between the first 102 and second 104 magnetic portions is selected to provide a characteristic electromagnetic emission from the magnetic resonance microstructure while in use. The size of the magnetic resonance microstructure 100 may be selected according to the particular application. In many applications, the magnetic resonance microstructure 100 has a maximum dimension that is less than about 5 mm. In certain specific applications, the structures may be as large as 5 mm to 5 cm, sizescales that match larger arteries, up to the largest artery, the aorta, that is typically 2 to 4 cm in diameter. Larger structures may be difficult to use or have limited applicability in human and/or animal subjects, for example. In some embodiments of the current invention, the magnetic resonance microstructure 100 can have a maximum dimension of at least about 10 nm and less than about 100 µm. For structures less than about 10 nm, they begin to approach molecular sizes. On the other hand, magnetic resonance microstructures less than about 100 µm can become particularly useful in micro-tagging applications, for example. In further embodiments of the current invention, the magnetic resonance microstructure 100 can have a maximum dimension of at least about 50 nm and less than about 10 µm. Magnetic resonance microstructures that are about 50 nm to a few hundred nanometers can facilitate cellular uptake in many biological, diagnostic and/or medical applications, for example. Magnetic resonance microstructures that are larger than about 10 µm can become less useful as contrast agents, for example. In certain cases, where the magnetic resonance structure may be used in fluid flow applications, for example like a magnetic stent, which through RF probing could yield information on the blood flowing through it, size scales may be up to a few cm diameter, corresponding to the size of the aorta. Also in certain fluid flow/imaging applications (described later) the sizes of the structures may be so large as to include the possibility of monitoring fluid flow through industrial scale pipes. However, the general concepts of the current invention are not limited to only these examples.

The term magnetic portion is intended to cover structures formed from magnetic and/or magnetizable materials. The term magnetic material is intended to include both permanent magnetic materials and magnetizable materials. For example, the magnetic portions may be formed from ferromagnetic, paramagnetic and/or superparamagnetic materials and/or alloys or compounds and/or combinations thereof, possibly together with nonmagnetic/weakly magnetic filler materials. For example, the magnetic elements comprising the magnetic resonance structures may be composed of nickel, iron, chromium, cobalt, manganese, various magnetic compounds such as various forms of iron-oxide, various forms of permalloy, mu-metal, etc. Additionally the magnetic elements may themselves represent hybrid elements that contain mixtures of magnetic and non-magnetic components including for example, layered materials that might alternate between a magnetic and non-magnetic layer, as well as, for example, conglomerations containing smaller particles of magnetic material material embedded within a host non-magnetic material. These examples are not meant to be exclusive; only to convey the notion that the magnetic elements should be material objects that either on their own, or once placed into a magnetizing field, exhibit a substantial magnetic moment. Note also that the term nonmagnetic is used throughout to distinguish from the ferro- and/or superparamagnetic materials, and does not necessarily imply a completely nonmagnetic substance, but rather one that is at most very weakly magnetic, often being very weakly paramagnetic or diamagnetic in nature. For example, the water commonly imaged/detected in MRI/NMR systems is of course detected because of its nuclear magnetism, but this is a much weaker magnetism and so we will refer to it throughout as being nonmagnetic. In some of the specific examples in this specification, magnetic portions are magnetized by an external magnetic field to alter the magnetic field between the magnetic portions. However, the general aspects of the current invention are not limited to only magnetic resonance microstructures that have magnetic portions constructed from magnetizable materials. In other embodiments, the magnetic portions may be constructed from permanent magnetic materials. In addition, the magnetic portions can be separate structures or can be formed integrally with other structures. Furthermore, the first 102 and second 104 magnetic portions can be separate structures in some embodiments, or may be different portions of an integral structure according to other embodiments. For example, there could be an additional one or two or more magnetic portions arranged relative to each other to form the substantially uniform magnetic field in the space 106 of FIG. 1. In other embodiments, instead of separate magnetic portions, the magnetic portions may be separate regions of a magnetic tube, for example. For example, if the magnetic portions 102 and 104 in FIG. 1 were imagined being rotated around an axis passing through the center of the reserved space 106, parallel to the magnetic field lines, this would represent a tubular magnetic structure that could be used in some embodiments of the current invention instead of separate magnetic portions. Also, spherical/elliptical shell-like magnetic structures could also be used in some embodiments of the current invention (although these embodiments would not accommodate the diffusion-based signal enhancement operation method unless the shells included some access hole(s)).

The magnetic resonance microstructure 100 can also have a spacer arranged between the first 102 and second 104 magnetic portions in some embodiments of the current invention (not shown in FIG. 1, see FIGS. 3 and 4 for example) or in some other embodiments this spacer may hold the first 102 and second 104 magnetic portions apart but be physically external to the space between those magnetic portions. The spacer is formed from a non-magnetic material in these embodiments. The spacer arranged between said first 102 and second 104 magnetic portions can maintain the space 106 reserved between the first 102 and second 104 magnetic portions such that it is open to permit a fluid to flow therethrough. Alternatively, in other embodiments of the current invention, the space 106 reserved between the first 102 and second 104 magnetic portions can be partially or completely filled with a nonmagnetic material that remains rather than flowing through. The spacer can have different properties in different environments, such as changes in surrounding pH, temperature, solution salinity etc. These properties can be utilized to effect a change in the magnetic field within the space to lead to detectable changes under observation with an MRI system. For example if the spacers were to expand or contract, the spacing between the two magnetic portions would increase or decrease thereby changing the magnitude of the field within the local homogeneous field region. Alternatively the spacers could decompose, or be disconnected, completely collapsing the structure and eliminating the internal homogeneous field region entirely. The microstructures can also have various nonmagnetic coatings applied to them. Such coatings may be useful for increasing structure rigidity, preventing material oxidation/corrosion, avoiding possible magnetic clumping of multiple structures by acting as a non-magnetic buffer zone between the structures, improving field uniformity by physically excluding access to select surrounding spatial volumes over which fields might be less uniform than desired, making structures less toxic by coating/sealing any toxic materials within a non-toxic coating, making structures biologically inert through, for example a titanium coating, making structures amenable to various bioconjugation protocols, for example through a gold coating, and/or varying structure hydrophobicity to enhance/diminish liquid flow through the structures. In additional they may also have a specific biochemical coating such as a specific ligand coating, for example, allowing for the microstructure to be targeted to a specific site and/or cell according to some embodiments of the current invention.

Additional embodiments of the current invention are directed to magnetic resonance imaging contrast agents that have a medium and one or more magnetic resonance microstructures dispersed in the medium. The medium can be a nonmagnetic liquid or gel, for example. The magnetic resonance structures can be the magnetic resonance structures 100 as described above with respect to some embodiments of the current invention. However, the magnetic resonance imaging contrast agents according to the current invention are not limited to including only the magnetic resonance structures 100. Other the magnetic resonance structures according to the current invention can also be used in alternative embodiments.

Figure 3:
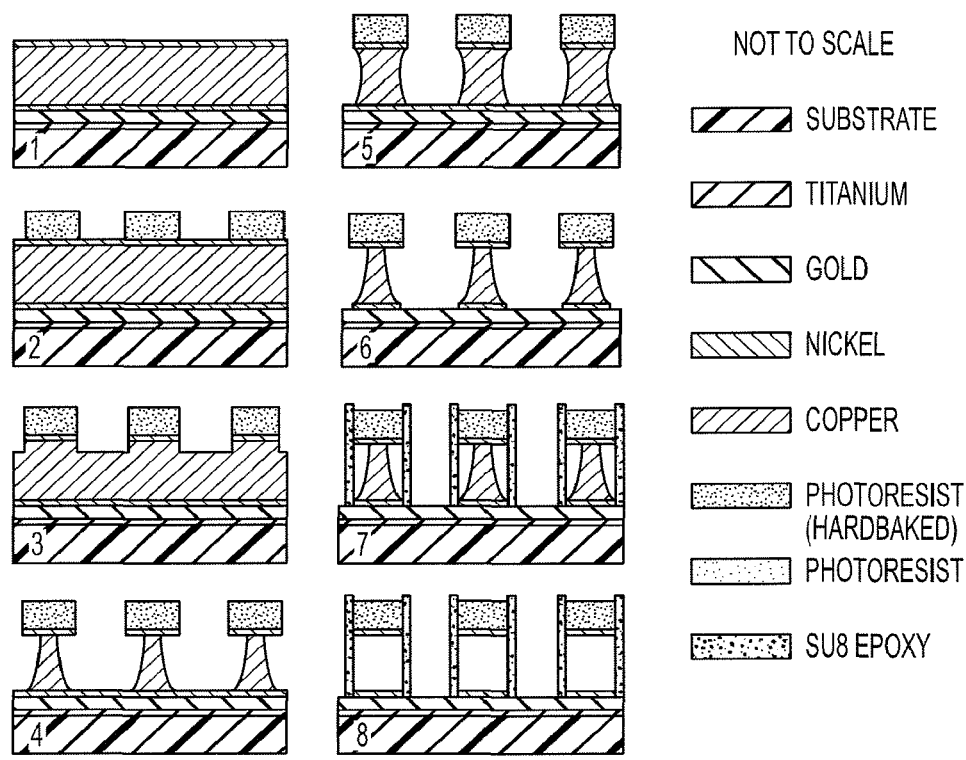
FIG. 3 is a schematic illustration of a method of manufacturing magnetic resonance microstructures according to an embodiment of the current invention.

FIG. 3 is a schematic illustration of one possible fabrication method to make magnetic resonance structures according to some embodiments of the current invention. This is only one of many possible fabrication methods and is illustrated here as an example. The manufacturing method of FIG. 3 can be summarized as follows:

Step 1: Evaporate titanium and gold onto a wafer substrate. Either electroplate or evaporate a nickel, copper, nickel sandwich.

Step 2: Spincoat, pattern, expose, develop, and hardbake photoresist so that it forms a permanent mask layer.

Step 3: Ion mill through top nickel layer and partway through copper layer.

Step 4: Wet etch copper down to the bottom nickel layer and stop before etching through the central copper support.

Step 5: Spincoat with photoresist and use the top nickel layer as a photomask so that subsequent photoresist flood exposure and development leaves photoresist remaining only between nickel layers. This protects the top nickel layer and patterns the bottom nickel layer for etching.

Step 6: Wet etch base nickel, and remove internal photoresist.

Step 7: Photopattern SU8 support posts.

Step 8: Wet etch away remaining copper

Figure 4A:
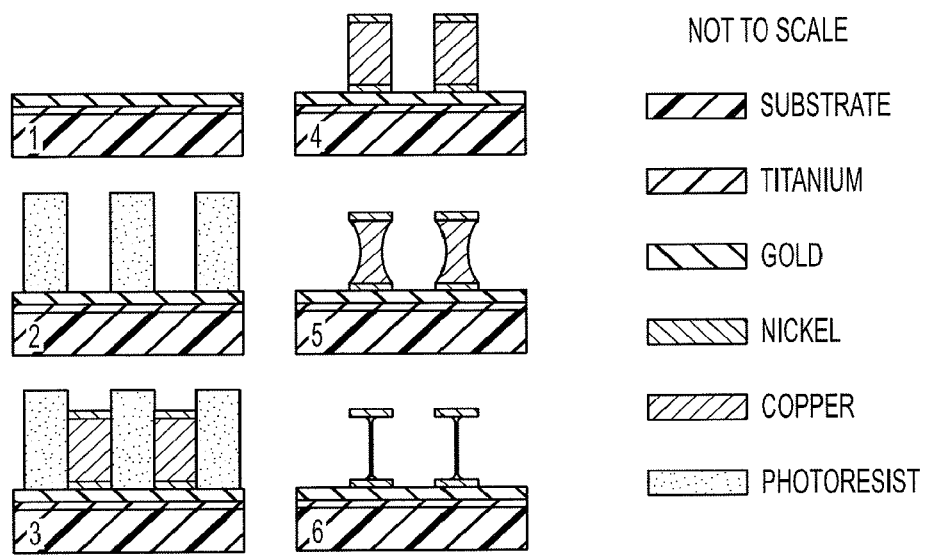
FIG. 4A is a schematic illustration of another method of manufacturing magnetic resonance microstructures according to an embodiment of the current invention.

FIG. 4A is a schematic illustration of another possible fabrication method to make magnetic resonance structures according to some embodiments of the current invention. The manufacturing method of FIG. 4A can be summarized as follows:

Step 1: Evaporate titanium and gold onto a wafer substrate.

Step 2: Spincoat and pattern thick photoresist.

Step 3: Electroplate nickel, copper, nickel into photoresist mold.

Step 4: Dissolve photoresist mold.

Step 5: Start a copper wet etch.

Step 6: Time copper wet etch "just right" so that it leaves central post.

Figure 4B:
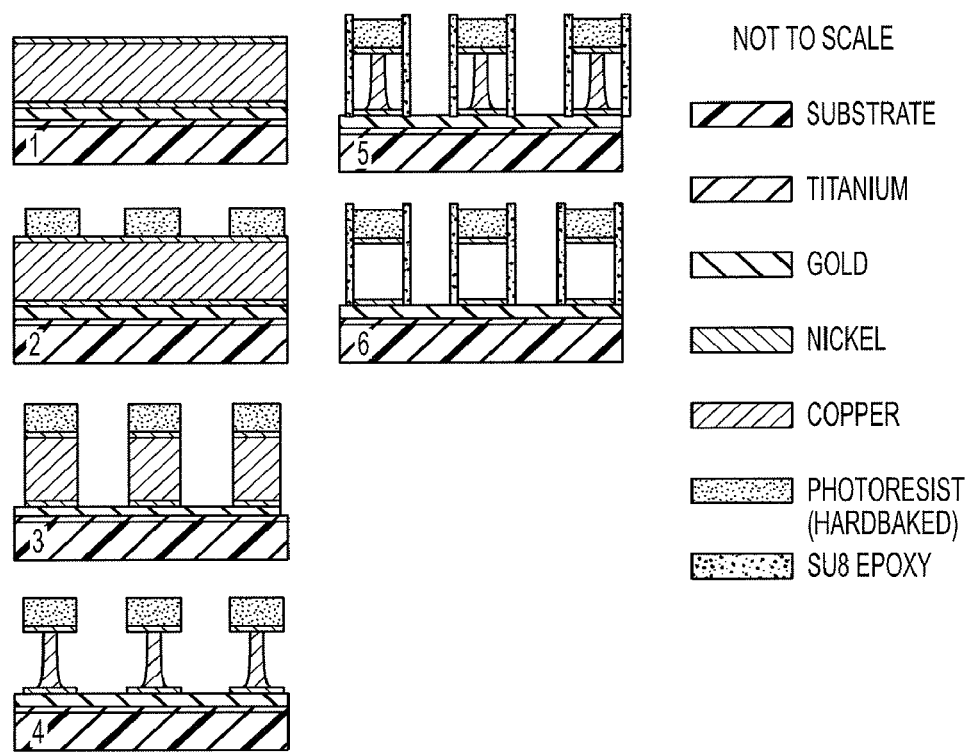
FIG. 4B is a schematic illustration of another method of manufacturing magnetic resonance microstructures according to an embodiment of the current invention.

FIG. 4B is a schematic illustration of another possible fabrication method to make magnetic resonance structures according to some embodiments of the current invention. The manufacturing method of FIG. 4B can be summarized as follows:

Step 1: Evaporate titanium and gold onto substrate wafer. Either electroplate or evaporate a nickel, copper, nickel sandwich.

Step 2: Spincoat, pattern, expose, develop, and hardbake photoresist so that it forms a permanent mask layer.

Step 3: Ion mill through the top nickel layer, through the copper layer, and through the base nickel layer, and follow with angled ion-mill to remove redeposited/resputtered material on the structure side walls.

Step 4: Wet etch copper part-way in to leave central support and stop at this point to leave single central post or continue to steps 5 and 6 to get external supports.

Step 5: Photopattern SU8 support posts.

Step 6: Wet etch away remaining copper.

Figure 4C:
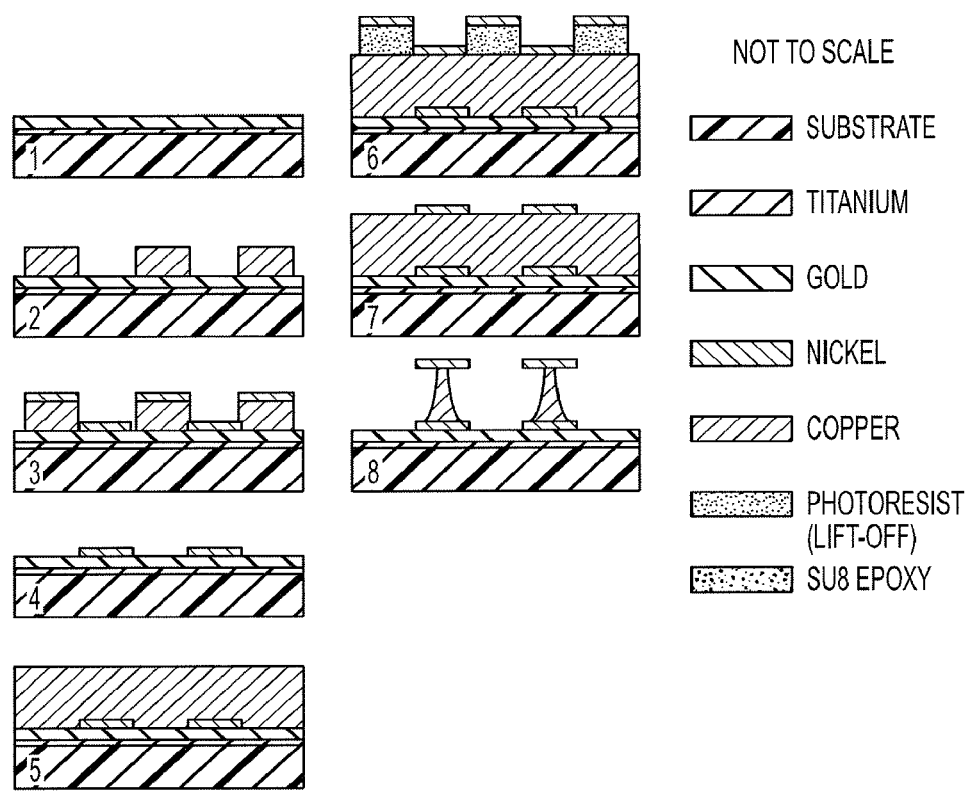
FIG. 4C is a schematic illustration of another method of manufacturing magnetic resonance microstructures according to an embodiment of the current invention.

FIG. 4C is a schematic illustration of another possible fabrication method to make magnetic resonance structures according to some embodiments of the current invention. The manufacturing method of FIG. 4C can be summarized as follows:

Step 1: Evaporate titanium and gold onto a wafer substrate.

Step 2: Spincoat, pattern, expose, develop, and lift-off photoresist layer.

Step 3: Evaporate nickel.

Step 4: Remove lift-off resist.

Step 5: Evaporate/electroplate copper.

Step 6: Repeat steps 2 and 3.

Step 7: Remove lift-off resist.

Step 8: Wet etch copper (or first cover nickel in another layer of patterned photoresist and do an ion-mill step prior to the wet etch).

Step 9: If wanted, proceed to add external posts and remove remaining copper.

Various alternative permutations and combinations of the steps shown in the sample fabrication procedures above could equally well be used to construct such objects and those exact steps and combinations thereof that are chosen, may depend on absolute structure sizes and aspect ratios. Such other manufacturing techniques and structures made thereby are included within the concepts of the current invention. The broad concepts of the current invention are not limited to magnetic resonance structures produced by only the above methods or to these specific methods of manufacture.

Figure 5:
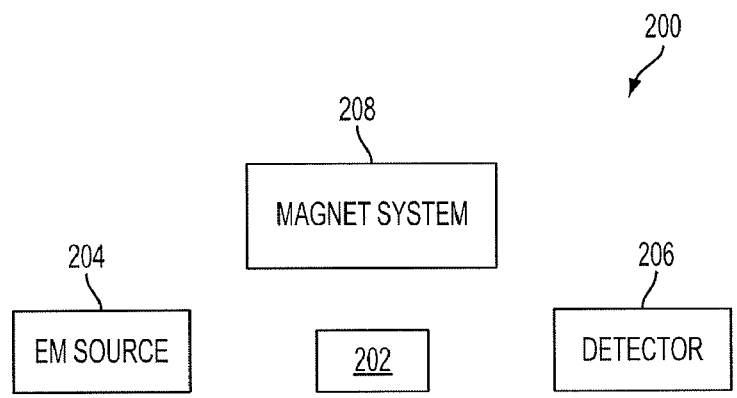
FIG. 5 is a schematic illustration of a magnetic resonance identity system according to further embodiments of the current invention.

FIG. 5 is directed to a magnetic resonance identity system 200 according to further embodiments of the current invention. The magnetic resonance identity system 200 has a magnetic resonance microstructure 202, a source of electromagnetic radiation 204 arranged to illuminate the magnetic resonance microstructure 202 with excitation radiation, and a detection system 206 constructed and arranged to detect electromagnetic radiation emitted from within the magnetic resonance microstructure 202 after the magnetic resonance microstructure 202 is illuminated with excitation radiation. The magnetic resonance microstructure 202 is constructed to absorb and emit electromagnetic radiation at a predetermined wavelength corresponding to a Larmor frequency of a nonmagnetic material arranged at least one of within or a part of the magnetic resonance microstructure 202. The magnetic resonance microstructure 202 can be, but is not limited to, magnetic resonance microstructure 100, for example. The magnetic resonance identity system 200 can also include a magnetic field generation system 208 arranged to provide a region of a magnetic field in which it is suitable to place a sample of interest. In one example, the magnetic resonance identity system 200 can be an MRI system with an MRI contrast agent according to an embodiment of the current invention. However, the magnetic resonance identity system 200 is not limited to only MRI systems.

Example 1

Among several possible configurations according to various embodiments of the current invention, we demonstrate a spaced, magnetizable double-disc geometry (see FIGS. 1,2 and 6-10) because in addition to generating a highly homogeneous field over a large volume fraction, its open design helps maximize water self-diffusion that, as discussed later, dramatically increases its signal-to-noise ratio (SNR) over that of any closed structure.

The double-disc geometry of this example is also inherently scalable and well-suited to massively parallel wafer-level microfabrication. Particle complexes can be surface micromachined in various different ways that may, for example, include various combinations of metal evaporation, sputtering, and electroplating depositions together with various wet and dry etching processes. The discs are separated via non-magnetic spacers: either an internal metal post that remains after a timed etch, or external lithographically-defined bio-compatible (Kotzar, G. et al. Evaluation of MEMS materials of construction for implantable medical devices. *Biomaterials* 23, 2737-2750 (2002); Voskerician, G. et al. Biocompatibility and biofouling of MEMS drug delivery devices. *Biomaterials* 24, 1959-1967 (2003)) photo-epoxy posts according to a couple of examples. A final gold sputter-coating can also be included to further enhance bio-compatibility and access to thiol-based chemistry for specific surface functionalization if desired.

While calculations of field homogeneity are necessarily numeric, the frequency shift, $\Delta\omega$, can be approximated analytically from the field at the centre of the structure. For gyromagnetic ratio, $\gamma$, and magnetically saturated discs of thickness, h, radius, R, centre-to-centre separation, 2S, and saturation magnetic polarization, $J_S$, elementary magnetostatics gives $\Delta\omega = (\gamma J_S/2) \cdot [(S-h/2)((S-h/2)^2+R^2)^{1/2} - (S+h/2)((S+h/2)^2+R^2)^{1/2}]$. For thin discs with $h \ll 2S \approx R$, this reduces to $$\Delta\omega \approx -\gamma J_S \cdot \frac{hR^2}{2(R^2+S^2)^{3/2}}.$$

Spectral signatures can be tailored by modifying any or all of $J_S$, h, R, and S. All particles shown in this specification were made from nickel ($J_S \approx 0.5$–$0.6$ T), but could equally well be formed from other magnetic alloys. $J_S$ can therefore be chosen anywhere from zero up to 2 Tesla (soft iron) enabling uniquely large water shift ranges from 0 to of order $-10$ MHz. This frequency-shifting ability implicitly assumes alignment between the disc planes and the applied magnetizing MRI field, $B_0$. Such alignment is ensured by the structure's built-in magnetic shape anisotropy (see FIG. 10). For any misalignment angles, $\theta$, between $B_0$ and the disc planes, resulting magnetic torques on the discs produce automatic self-aligning pressures of approximately $(h/(R^2+S^2)^{1/2}) \cdot (J_S^2/4\pi \cdot 10^{-7} \text{ Hm}^{-1}) \cdot \sin(2\theta)$, equating to of order $10^{-8}$ to $10^{-6}$ N/$\mu m^2$. By comparison, even within cellular cytoplasm, yield stresses are only in the $10^{-13}$ to $10^{-9}$ N/$\mu m^2$ range (Sato, M., Wond, T. Z. & Allen, R. D. Rheological properties of living cytoplasm: endoplasm of *physarum plasmodium*. *J. of Cell. Biol.* 97, 1089-1097 (1983); Ashldn, A. & Dziedzic, J. M. Internal cell manipulation using infrared laser traps. *Proc. Natl. Acad. Sci.* 86, 7914-7918 (1989)).

Unlike chemical shifting, the frequency dependence on a dimensionless geometrical aspect ratio implies shifting of any nuclear species and by any overall particle size. For example, in the following examples we demonstrate frequency shifting of both hydrogen and deuterium nuclei and by particle size scales spanning three orders of magnitude from millimeter to micrometer.

Being externally similar to MPIOs with comparable dipolar far-field decays, the structures can be spatially imaged using the same dephasing common to MPIOs; but in addition they can be differentiated spectrally and distinguished from spurious signal voids that confound SPIO/MPIO imaging. Depending on particle size, multiple different particle spectra can be acquired simultaneously from a single free induction decay following a hard $\pi/2$ excitation. Alternatively, chemical shift imaging can spatially and spectrally resolve the tags simultaneously (see FIG. 11).

Figure 11:
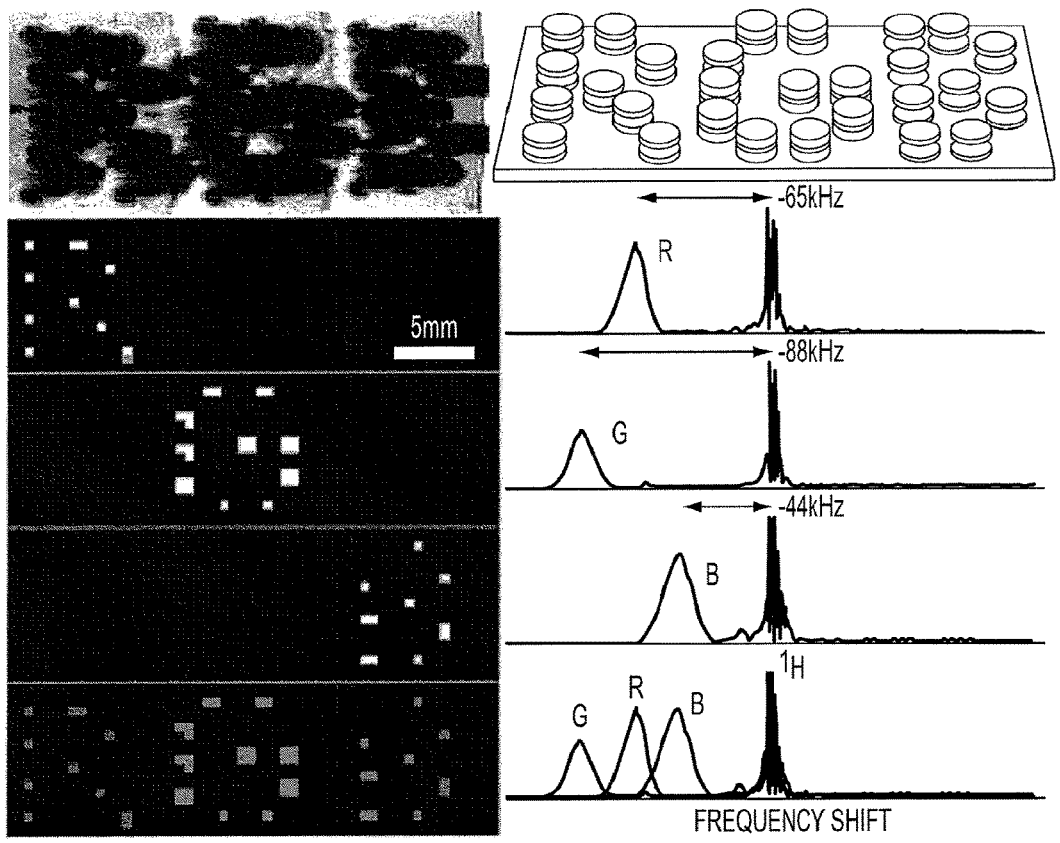
FIG. 11 shows chemical shift imaging (CSI) of demonstration 1.25 mm-diameter particles magnetized by $B_0$ according to an embodiment of the current invention.

FIG. 11 shows chemical shift imaging (CSI) of demonstration 1.25 mm-diameter particles magnetized by $B_0$ according to an embodiment of the current invention. Particle frequency was varied by changing the thickness of electroplated nickel layers that formed the magnetizable disc pairs, shown schematically (not to scale) at top right. As with regular SPIO detection, magnetic dephasing due to the particles' external fields enables the spatial imaging shown in the gradient-echo (GRE) MRI at top left. However, comparison between the GRE and CSI images below, shows that the additional spectral information both differentiates between particle types and improves particle localization. With particle spectra (shown alongside to the right) shifted well clear of the water proton line, different planes in the CSI map isolate different particle types for unambiguous color-coding with minimal background interference (bottom panel). (While still visible in the GRE image, the top corner particle of the letter "B" was damaged causing its shifted frequency peak to vanish).

Direct spectral imaging, however, is fundamentally limited by the relatively small number of nuclei contributing to the signal. Whether from some encapsulated frequency-shifted water protons or from different nuclei altogether (Lanza, G. M. et al. $^1$H/$^{19}$F magnetic resonance molecular imaging with perfluorocarbon nanoparticles. Current Topics in Devel. Bio. 70, 57-76 (2005)), the signal is proportional to the particle volume. Our open structures, however, allow also a highly efficient analogue to magnetic transfer imaging (Henkelman, R. M., Stanisz, G. J. & Graham, S. J. Magnetization transfer in MRI: a review. NMR Biomed, 14, 57-64 (2001)) with diffusional exchange between water inside and outside the particle replacing traditional chemical exchange between bound and free protons. Therefore, using a preparatory set of π/2 pulses at the particle's shifted resonance to saturate out signal from a subsequent on-resonance pulse, the continual diffusion of fresh spins through the open particle structure can multiply its apparent signal volume. Scanned over off-resonant frequencies, this yields the so-called z-spectra (Grad, J. & Bryant, R. G. Nuclear magnetic cross-relaxation spectroscopy. J. Magn. Reson. 90, 1-8 (1990)) shown in FIGS. 13-16. Because the required time, $\tau_d$, for self-diffusion to "refresh" the internal water scales with $R^2$, the saturated magnetization falls only linearly with R, not with volume~$R^3$, as particle size is reduced. Without diffusion, the effective "refresh" time would be limited to of order the longitudinal relaxation time, T1≈2-3 seconds. For water self-diffusivity, D=2.3·10$^{-9}$ ms$^{-2}$, the distance diffused during this time, $(6D·T1)^{1/2}$≈0.2 mm, effectively sets the size below which open structures gain. This size is two orders of magnitude larger than typical micrometer-sized particles that might be used for cell labeling, implying SNR gains from diffusion through micrometer-sized open structures of order 10$^4$.

Figure 17:
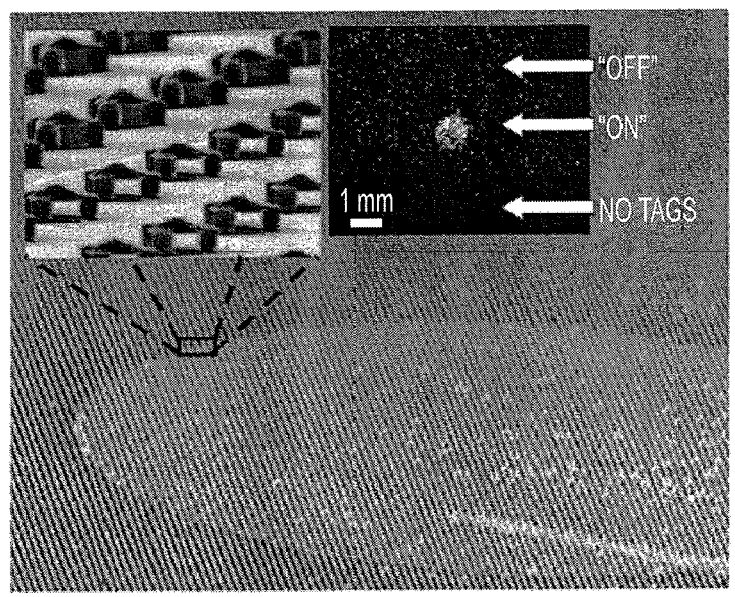
FIG. 17 shows high tilt angle SEM showing a square array of R=2.5 μm particles according to an embodiment of the current invention. Except for a defined circular region, all particles have their interiors filled, blocking water diffusion. The insets show the boundary between "open" and "closed"

The double-disc structures provide a specific demonstration of this principle. With their high shifted-field homogeneity, background signal can be suppressed while still saturating out about ⅓ of the volume between the discs via off-resonant excitation pulses with bandwidths just a few percent of the particle's shift (see FIG. 6). For equilibrium B$_0$-aligned magnetization, M$_0$, and h<<2S≈R, the magnetic moment of the water saturated in a single pulse is $m_{pulse}$≈M$_0$πR$^3$/3. Since not all the water exchanges between consecutive pulses, however, this per-pulse magnetic saturation falls with subsequent pulses. For an inter-pulse delay, $\tau_d$=R$^2$/6D, simulations show a resulting per-pulse average saturation of about $m_{pulse}$/2. The spatial distribution of any single pulse of saturated magnetization at some later time, t>>$\tau_d$, can be approximated by analogy to an instantaneous point-source diffusion problem, giving: $M_S(r,t)≈(m_{pulse}/2)·(4\pi Dt)^{-3/2}·\exp(-r^2/4Dt)·e^{-t/T1}$, where the final factor accounts for relaxation back into alignment with B$_0$ and r measures distance from the particle. Within a characteristic diffusion distance, d≡(D·T1)$^{1/2}$, a $\tau_d$-spaced train of such pulses rapidly (order T1) asymptotes to a steady-state distribution, $M_S(r)≈(M_0/4)·(R/r)·e^{-r/d}$. Integrating over a (spherical) voxel of radius R$_v$>>R with R$_v$<d, then gives the approximate magnetization reduction surrounding the particle, $M_S/M_0$≈0.4·R/R$_v$, highlighting the diffusion-enabled linear rather than cubic scaling that boosts SNR. For example, although the resonant field volume of an R=2.5 μm particle shown in FIG. 9 constitutes just 0.003% that of a 50 μm radius voxel, it can saturate out of order a thousand-fold larger 2% of the voxel, potentially enabling simultaneous single particle imaging and spectral identification (as suggested in FIG. 17) while obviating the need for any specialized micro-coils (Olson, D. L., Peck, T. L., Webb, A. G., Magin, R. L. & Sweedler, J. V. High-resolution microcoil $^1$H-NMR for mass-limited nanoliter-volume samples. Science 270, 1967-1970 (1995)); indeed, all imaging in this example was done with macroscopic surface and solenoidal RF coils up to several centimeters in diameter.

To compare the micro-engineered approach with traditional chemically-synthesized molecular and nanoparticle agents, we turn attention from individual particle identification to detectable concentrations. In terms of total agent volume, here a larger number of smaller particles is preferable to a smaller number of larger ones, but already within photolithographic limits, micrometer-sized particles yield low concentration requirements. Including continual longitudinal relaxation, the magnetic moment saturated out per particle pulsed over a time t=2T1 is $(m_{pulse}/2)·(T1/\tau_d)·(1-e^{-2})$. Because SNR varies with imaging volume, we conservatively assume at least 5% fractional saturation for reliable detection. This yields a required particle concentration of order 10$^{-14}$ M or, in elemental terms (assuming iron discs of similar aspect ratios to those of the particles in FIG. 8), 0.01 mmol Fe/l. This concentration is far below typical chemical exchange agent concentrations (Woods, M., Woessner, D. E. & Sherry, A. D. Paramagnetic lanthanide complexes as PARACEST agents for medical imaging. Chem. Soc. Rev. 35, 500-511 (2006)), an order of magnitude less than the clinical dosages of gadolinium relaxivity-based contrast agents (Runge, V. M. & Wells, J. W. Update: safety, new applications, new MR agents. Topics in Magn. Reson. Imaging 7, 181-195 (1995); Shellock, F. G. & Kanal, E. Safety of magnetic resonance imaging contrast agents. J. Magn. Reson. Imaging 10, 477-484 (1999)), and equal to those of SPIO agents (Weissleder, R. et al. Ultrasmall superparamagnetic iron oxide: characterization of a new class of contrast agents for MR imaging. Radiology 175, 489-493 (1990)). Further, since administered gadolinium and SPIO agents are not spread evenly throughout the body, 0.01 mM is actually far below the real detected concentrations of these agents.

Since required concentrations scale with $R^2$, deep-UV or electron-beam lithography can substantially further reduce this limit. Ultimately, useful particle size is limited not by lithography, but by $\tau_d$. In analogy to the "slow-exchange" restriction (Woods, M., Woessner, D. E. & Sherry, A. D. Paramagnetic lanthanide complexes as PARACEST agents for medical imaging. Chem. Soc. Rev. 35, 500-511 (2006)) on chemical exchange processes, here diffusional exchange should not be so fast as to broaden the spectral peak by more than its shift. Fortunately, because the particles can generate large shifts, this exchange-broadening becomes fundamentally limiting only below the 100 nm scale, where required metal concentrations are in the nanomolar regime. The faster imaging and increased safety margins that these low concentration requirements imply are a consequence not only of faster allowable exchange rates, but also of the extended homogeneous field regions that can exchange many spins simultaneously, as opposed to the individual exchangeable proton sites of molecular complexes (Woods, M., Woessner, D. E. & Sherry, A. D. Paramagnetic lanthanide complexes as PARACEST agents for medical imaging. *Chem. Soc. Rev.* 35, 500-511 (2006)). Micro-engineering also enables biologically benign material choices making these field regions directly accessible, eliminating chelated lanthanide-ion-based agents' efficiency-versus-toxicity trade-offs (Runge, V. M. & Wells, J. W. Update: safety, new applications, new MR agents. *Topics in Magn. Reson. Imaging* 7, 181-195 (1995); Shellock, F. G. & Kanal, E. Safety of magnetic resonance imaging contrast agents. *J. Magn. Reson. Imaging* 10, 477-484 (1999)). Additionally, using ferro- or superparamagnetic materials ensures full saturation even for small $B_0$, enabling lower imaging fields while retaining large, field-independent shifts (see FIG. 14); sensitivity does however improve with increasing field due to the increasing T1.

In principle, spectrally distinct physiological "smart" indicators can also be formed by either encapsulating the particles, or filling their internal regions, to inhibit internal diffusion (see FIG. 17), while leaving their external spatially trackable image-dephasings unaffected. With the inhibiting material chosen vulnerable to specific enzymatic attack, or to dissolution beyond a certain temperature or pH, subsequent water diffusion could effectively "turn on" their spectral signals. Conversely, the spacer elements could be made from some dissolvable or reactive material to effectively modify, or completely "turn off" the spectral signals. Orientationally-dependent sensors should also be possible by varying geometry to decrease magnetic self-alignment, yielding signals that appear or disappear depending on particle orientation. Such orientation sensing may be useful, for example, for mapping fluid flow direction or for measuring fluid flow strength. For example, if fluid forces were stronger than magnetic self-alignment forces, then structure orientation, and hence the existence of the spectral signature, would depend on fluid flow direction. In this way, vasculature network geometries, too small to normally be seen with MRI, could potentially be mapped out. Also, fluid flow strength could measured by observing whether or not the fluid can realign the structures. With spectral differentiation enabling multi-particle co-registration within the same voxel, a variety of multiplexed diagnostics can be envisioned. Additionally, their open structures and large shift ranges are well-suited for flow and perfusion studies with multiple spin-labeled streams immune to magnetic mixing. Moreover, beyond MRI altogether, their sub-cellular size permits the possibility of RFID-based microfluidics.

Engineering local field environments over sub-cellular size-scales through tailored microstructures appears a promising new avenue to a variety of sensitive new imaging and/or detection mechanisms. Particularly encouraging are the design latitudes afforded by micro-engineering's large SNR gains over traditional chemical synthesis, raising the prospect for a multiplicity of additional microstructures that may similarly increase MRI functionality and impact.

Methods

Apart from the magnetic self-alignment experiments that involved freely floating particles in water, to enable more precise analysis, control experiments were performed on grids of test particles (13×13 mm square) on diced 15×15 mm pyrex substrates on which the particles were originally microfabricated. Inter-particle spacings (centre-to-centre) were typically 3 to 4 times the particle diameter at which point any influence from the external fields of neighbouring particles had decayed to negligible levels. Individual pyrex chips were placed in custom-made holders filled with a layer of water or deuterium oxide ~150 μm thick, sufficient to deeply submerge the particles and to continue well beyond the extent of any appreciable external particle field decays. Single water- or deuterium oxide-submerged pyrex chip samples were then placed next to, or inside of, surface or solenoidal coils for transmission/reception of the NMR signal.

For the direct spectral detection experiment using water (spectra of FIG. 11), free induction decay (fid) signals following a spin-echo were acquired sweeping through a range of frequencies covering the expected offsets produced by the particles. Shaped pulses with a Gaussian profile were used to limit bandwidth spread into the bulk water peak (as compared to a hard pulse). Their bandwidths were however sufficient to cover the frequency profiles produced by the particles. Acquisitions for the spectra were 8192 points in length, covering a bandwidth of ~100 kHz. For the associated RGB image, three 2D chemical shift images were acquired, covering the frequency ranges of the particle spectra. Images are integrations of the spectra over the different frequency ranges. In-plane resolution was 500×750 μm. Particle geometrical parameters were {R, 2S, h}≈{625 μm, 500 μm, [4, 6, 8] μm} Accidental impurities in the nickel discs of these structures led to a reduced $J_s$≈0.4 T. (All other structures had pure nickel with $J_s$≈0.5-0.6 T)

Figure 12:
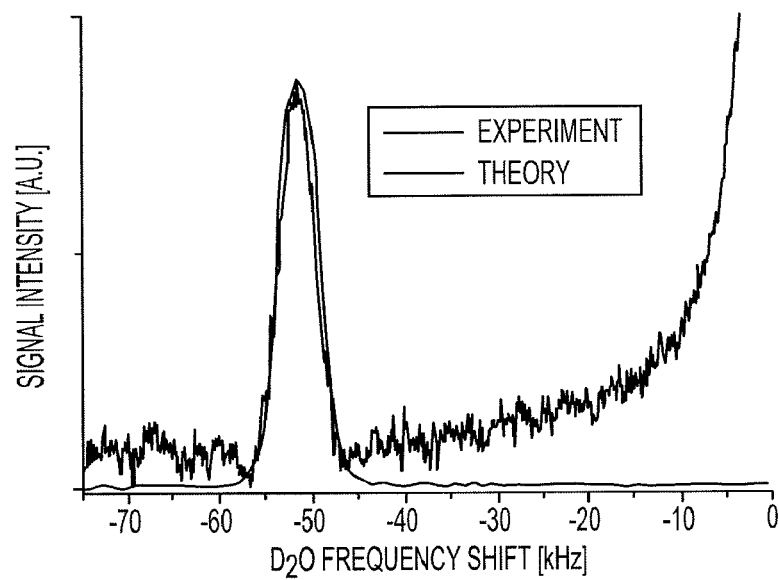
FIG. 12 shows Fourier transformed spin-echo signal, showing direct imaging at 11.7 T of spectrally shifted deuterium oxide peak from a set of R=12.5 μm particles submerged in $D_2O$ according to an embodiment of the current invention. Apart from overall signal magnitude, there are no free theory fitting parameters.
Figure 13:
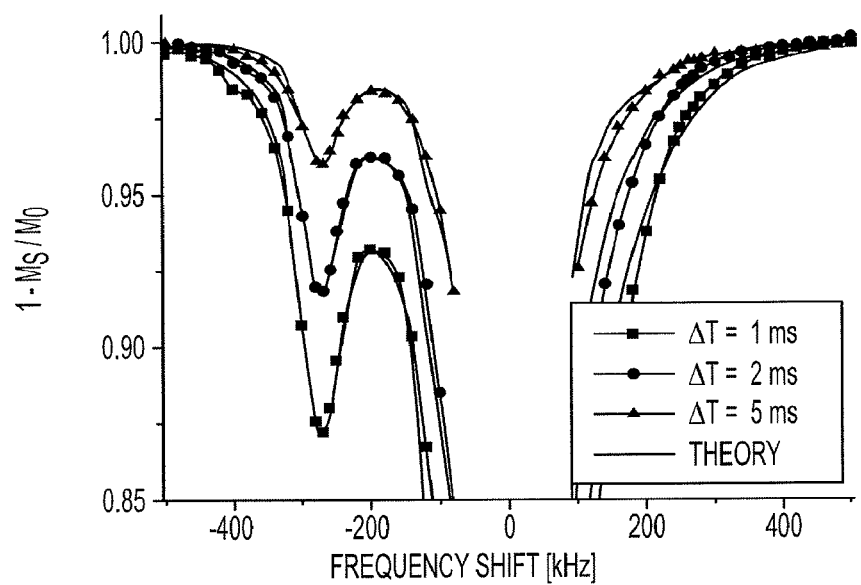
FIG. 13 shows R=2.5 μm particle $H_2O$ z-spectra taken at 7 T showing increasing signal with shortening delays, $\Delta T$, between off-resonant $\pi/2$ pulses according to an embodiment of the current invention. Overlaid theory is derived from first-principles Monte Carlo simulation and contains no free fitting parameters.
Figure 14:
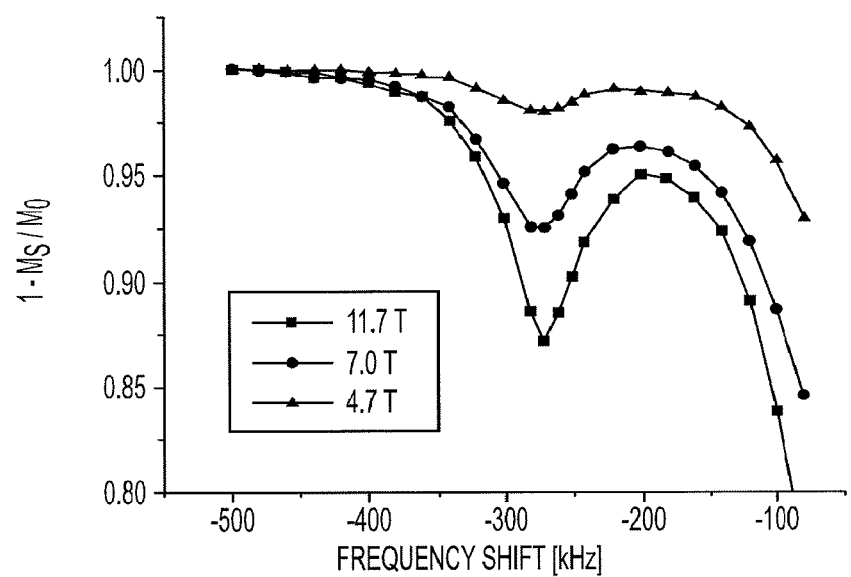
FIG. 14 shows R=2.5 μm particle $H_2O$ z-spectra for $\Delta T=2$ ms at three different field-strengths, showing frequency shifting independent of $B_0$ according to an embodiment of the current invention.
Figure 15:
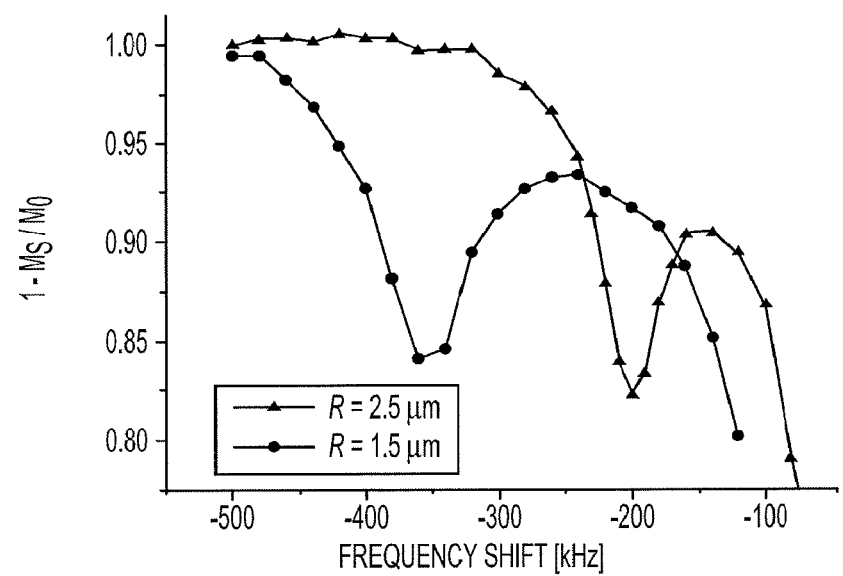
FIG. 15 shows $H_2O$ z-spectra demonstrating different frequency shifts from structures with different R's, but with fixed h=50 nm and approximately constant S/R≈0.3–0.4 according to some additional embodiments of the current invention. Because assembled data of FIGS. 14 and 15 are from different MRI magnets and coils, comparative theory overlays are less meaningful, but the data remains in agreement with theory.
Figure 16:
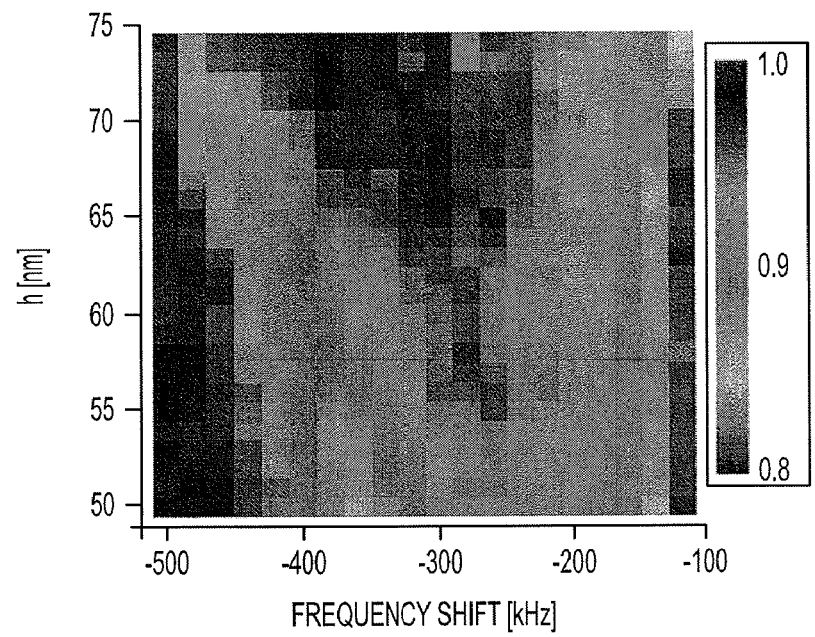
FIG. 16 shows continuous frequency-pulling engineered through continuously changing h (each row in the image shows the experimental $H_2O$ z-spectrum for a different particle disc thickness according to embodiments of the current invention). For completeness we show everywhere raw z-spectra of the shifted peaks atop the unshifted broadened water background; because the surrounding water broadening is approximately symmetric, however, this background can be eliminated by considering differences between corresponding positive- and negative-frequency saturations. All data is from first-generation test particles and possible sub-optimal geometries and ~10% inter-particle frequency-shift variation due to cross-wafer manufacturing variation. Improved fabrication should be able to reduce variation to below 1%, substantially narrowing the linewidths and increasing the saturation levels.

For the direction detection experiment using $D_2O$ (FIG. 12), fids following a spin-echo were acquired using as large a bandwidth as our coil would allow ~50 kHz. Particle geometrical parameters were {R, 2S, h}≈{12.5 μm, 10 μm, 0.5 μm}.

For the indirect detection experiments (FIGS. 13-16), the pulse sequence consisted of a series of off-resonance pulses (Gaussian shape, 100 μs in length) for a period of a few T1's, preceding an on-resonance 90-degree pulse for collection of an fid. Each point in the z-spectra represents the integral of this fid for a different off-resonance frequency of the preparatory pulse train. The gap between each pulse in the preparatory pulse trains was varied between 1 ms and 5 ms. For experiments at different field strengths (4.7, 7, 11.7 T), differing $B_1$ profiles from the different coils used may have led to some variations in the results. Particle geometrical parameters were {R, 2S, h}≈{2.5 μm, 2 μm, 65 nm} for FIGS. 13,14, and {R, 2S, h}≈{2.5 μm, 2 μm, 50 nm} and {1.5 μm, 1 μm, 50 nm} for FIG. 15.

To demonstrate the imaging using the indirect detection (FIG. 17), gradient-echo images were acquired after a series of pulses at the pre-determined offset frequency (in this case −330 kHz). A baseline image without the preparatory sequence was used to provide a subtraction image. The in-plane image resolution was 100×100 μm with the thickness being determined by the depth of the water ~150 μm. To speed up the imaging, the TR was set to 500 ms with the preparatory sequence being run continuously between each TR. Particle geometrical parameters were {R, 2S, h}≈{2.5 μm, 2 μm, 80 nm}. Variation in particle parameters was dominated by variation in the thickness of the nickel disc layers of about 10% throughout.

Example 2

In this example according to some embodiments of the current invention, we consider a simple, yet generalizable, resputtering technique on top-down photolithographically prepatterned substrates. Often regarded as an undesirable by-product of ion milling, redeposited back-sputtered material is here instead exploited to yield scalable, large-area, parallel fabrication of accurately defined free-standing nanostructures. Demonstrating the added functionality that such top-down definition can permit, a new form of MRI label is introduced: cylindrical magnetic nanoshells that can function both as conventional $T_2^*$ and as new spectral-shifting, or "color", contrast agents. These labels, which are hollow cylinders formed from nanometers-thick shells of magnetizable material, can both modulate local magnetic resonance relaxivities as well as generate controlled, tunable nuclear magnetic resonance (NMR) shifts in the surrounding water through precise control of the shell heights, radii and wall thicknesses.

With function determined by form, the shell geometrical dependences are first explained before detailing the shell fabrication. Although hollow cylinders clearly differ from flat disks (see examples above and Zabow, G.; Dodd, S.; Moreland, J.; Koretsky, A. *Nature* 2008, 453, 1058), the physical basis behind these new cylindrical nanoshells' spectral shifting properties can be understood, as described below, through a simple transformation as analogous to that behind the double-disk structures described above.

For proton gyromagnetic ratio $\gamma$, the Larmor precession frequency $\omega$, of water hydrogen protons in a magnetic field of magnitude B, is given by $\omega = \gamma B$. In the vicinity of any magnetic structure, therefore, proton precession frequencies vary proportionally to the spatially varying magnetic fields produced by that structure. Accordingly, NMR spectra integrating over water proton signals from around that structure would typically integrate over broad frequency ranges, leading to broadened water lines. To yield instead a distinct frequency-shifted NMR peak, the magnetic structure geometry must be such that it produces a water-accessible, extended spatial volume over which the total field from the magnetized structure's field together with the applied magnetizing background MRI field $B_0$, is homogeneous and distinct in magnitude from the surrounding fields. We have shown in the above examples that the field between two suitably spaced magnetized disks possesses the necessary homogeneity to yield such shifted NMR peaks. In such a double-disk system, the disks are assumed aligned such that the $B_0$ field vector is parallel to the disks' planes. However, this alignment requirement restricts orientation about only a single axis; in particular, the double-disk structure is free to rotate about a central axis parallel to $B_0$. Because the resulting NMR frequency shifts are invariant with respect to this rotation, a variety of alternative structures, each composed of what can be regarded as superpositions of rotated double-disk structures, should also possess the appropriate homogeneous field profiles. Although a hollow cylinder represents the surface of revolution of a radially-offset thin rectangle, rather than that of a disk, its similarity to a rotated double-disk system means that its internal fields can likewise generate distinct spectrally shifted NMR peaks.

FIGS. 18a-18c show a schematic illustration of a cylindrical shell magnetized to saturation by $B_0$, together with resulting numerically calculated magnetic field magnitude profiles demonstrating the shell's homogeneous internal field. The histogram in FIG. 18d records the calculated field magnitudes (or equivalently, proton precession frequencies) throughout the space around the shell. By showing the relative volumes of space corresponding to each precession frequency, or field magnitude, the histogram approximates the resulting NMR spectrum from water in the shell's vicinity. The shifted spectral peak evident in the histogram is due to the shell's internal homogeneous field region whose spatial extent is delineated by the surface contour plot of FIG. 18e.

The shifted resonance linewidth is determined by the internal field homogeneity which depends on shell geometry as shown in FIGS. 19A and 19B. Although the shell walls may have high aspect ratios, the overall cylindrical shell is fairly short, with an optimal length-to-diameter ratio just above unity. For such a shell the NMR frequency shift $\Delta\omega$, of the water within it can be analytically approximated from the field at its center. Assuming a magnetically saturated cylindrical shell of material with saturation magnetic polarization $J_s$, wall thickness t, diameter $2\rho$, and length L, the frequency shift is $\Delta\omega = \gamma J_s L \cdot [(L^2+(2\rho+t)^2)^{-1/2} - (L^2+(2\rho-t)^2)^{-1/2}]$. Simplifying to a thin-walled structure ($t \ll L \approx 2\rho$) gives:

$$\Delta\omega \approx -4\gamma J_s \left( \frac{L\rho t}{(L^2 + 4\rho^2)^{3/2}} \right). \qquad (1)$$

Equation (1) shows that shell frequency shifts can be engineered by varying shell lengths, radii, wall thicknesses, and material compositions. In this way, the different spectral signatures of different cylindrical shells can be regarded as MRI radio-frequency analogs to the different optical colors of different quantum dots (Bruchez, M. Jr.; Moronne, M.; Gin, P.; Weiss, S.; Alivisatos, A. P. *Science* 1998, 281, 2013; Chan, W. C. W; Nie, S. *Science* 1998, 28/, 2016). Here, however, it is shell geometry, rather than dot size, that determines the spectral response. Indeed with all geometrical parameters combining into a dimensionless ratio, the shells' magnetic resonance frequencies are controlled specifically by structure geometry but are independent of overall size. Provided all dimensions are scaled proportionally, therefore, nanoscale shells can shift the surrounding water NMR frequencies by just as much as can shells that may be far larger. A fabrication method that offers independent control over each dimension, and that is scalable across a wide size range, is therefore desirable for increasing the range of applications of the resulting frequency-shifting agents according to some embodiments of the current invention. Particularly advantageous for some embodiments is scalability down to the nano-regime. Apart from smaller structures affording increased biological compatibility, relative to their size, smaller shells can amplify signals to a larger degree than can larger shells. This signal gain with structure miniaturization is due to water self-diffusion that, over typical proton relaxation periods, becomes appreciable on the micro- and nano-scales and that therefore enables signal amplification through magnetization transfer techniques (Zabow, G.; Dodd, S.; Moreland, J.; Koretsky, A. *Nature* 2008, 453, 1058; Zurkiya, O.; Hu, X. *Magn. Reson. Med.* 2006, 56, 726; Henkelman, R. M.; Stanisz, G. J.; Graham, S. J. *NMR Biomed.* 2001, 14, 57) that exploit the continual exchange of water between inside and outside the shell. The smaller the structure, the more rapid is this water exchange. As such, for equal total quantities of magnetic material used to construct an ensemble of shells, an ensemble containing a greater number of smaller shells can interact with a larger volume of water than can an ensemble comprising a smaller number of larger shells. Provided the diffusional exchange is not so fast as to frequency-broaden the spectral peak by more than its shift, signals can increase quadratically as structure sizes shrink (Zabow, G.; Dodd, S.; Moreland, J.; Koretsky, A. *Nature* 2008, 453, 1058).

Beyond scalability, the fabrication method should also exhibit minimal cross-structure variation. If not, geometrical or compositional variations can induce unintended frequency shifts from one structure to the next, broadening and degrading the spectral peaks from signals integrated over ensembles of nanostructures. Indeed, ensuring optimally sharp magnetic resonances (Zabow, G.; Koretsky, A. P.; Moreland, J. *J. Micromech. Microeng.* 2009, 19, 025020)

demands monodispersity levels that may be at odds with those of typical bottom-up synthesized structures. As such, even though porous membrane templating techniques (Martin, C. R. *Science* 1994, 266, 1961) commonly used for synthesizing various cylindrical nanostructures such as rings, cones, tubes, rods, wires, and cables (Hobbs, K. L.; Larson, P. R.; Lian, G. D.; Keay, J. C.; Johnson, M. B. *Nano Lett.* 2004, 4, 167; Dickey, M. D.; Weiss, E. A.; Smythe, E. J.; Chiechi, R. C.; Capasso, F.; Whitesides, G. M. *ACS Nano* 2008, 2, 800; Wang, S.; Yu, G. J.; Gong, J. L.; Li, Q. T.; Xu, H. J.; Zhu, D. Z.; Zhu Z. Y. *Nanotechnology* 2006, 17, 1594; Yoo, W-C.; Lee, J-K. *Adv. Mater.* 2004, 16, 1097; Hua, Z.; Yang, S.; Huang, H.; Lv, L.; Lu, M.; Gu, B.; Du, Y. *Nanotechnology* 2006, 17, 5106; Bao, J.; Tie, C.; Xu, Z.; Zhou, Q.; Shen, D.; Ma, Q. *Adv. Mater.* 2001, 13, 1631; Sander, M. S.; Tan, L-S. *Adv. Funct. Mater.* 2003, 13, 393; Wang, Q.; Wang, G.; Han, X.; Wang, X.; Hou, J. G. *J. Phys. Chem. B* 2005, 109, 23326; Lahav, M.; Weiss, E. A.; Xu, Q.; Whitesides, G. *M. Nano Lett.* 2006, 6, 2166; Zhao, S.; Roberge, H.; Yelon, A.; Veres, T. *J. Am. Chem. Soc.* 2006, 128, 12352), can sometimes yield what may be, by bottom-up standards, relatively monodisperse features, top-down patterning's enhanced dimensional control and inter-particle uniformity can render it a more favorable approach.

Because the nanoscale lateral definition demanded by the cylindrical shells' high-aspect-ratio walls is poorly suited to traditional planar microfabrication, however, we introduce an unconventional approach based on local resputtering of a prepatterned substrate. The key step to this fabrication method is straightforward, involving ion-milling away a thin magnetic layer previously evaporated onto a substrate patterned with an array of solid cylindrical posts. During this ion-milling, a fraction of the magnetic material emitted from the substrate redeposits on the post sidewalls, leaving cylindrical magnetic nanoshells once the post material has subsequently been dissolved. While the process itself may be simple, less simple is why it should be well-suited to producing nanoshells with just the right properties to yield well-defined NMR spectral peaks. In particular, sharp resonances require shells with uniform wall thicknesses over their full lengths (see FIG. 19B).

FIG. 20A sketches the geometry used for discussion of the sputter-coated wall thickness as a function of height z, up the side of a cylindrical post. Naively, one might expect the sputtered coating to be much thicker at the base of the post than at its top since points near the post's base are closer to the source of sputtered substrate atoms than are points higher up on the post. This is not the case, however, because the sputtered atom distribution is not isotropic. According to linear collision cascade theory (Sigmund, P. *Phys. Rev.* 1969, 184, 383; Behrisch, R. (ed). Sputtering by particle bombardment I. *Physical sputtering of single-element solids*; Springer-Verlag: Berlin, 1981) sputter distributions are, to first order, proportional to cos θ, for θ the angle between the sputtering direction and the substrate normal. Specifically, experiments (Behrisch, R. (ed). Sputtering by particle bombardment I. *Physical sputtering of single-element solids*; Springer-Verlag: Berlin, 1981; Behrisch, R.; Wittmaack, K. (eds). *Sputtering by particle bombardment III. Characteristics of sputtered particles, technical applications*; Springer-Verlag: Berlin, 1991) have shown that sputter distributions vary from under-cosine, to cosine-like, to over-cosine as incident ion energies increase. Angular dependences are therefore generally approximated as proportional to $\cos^m \theta$, with values of m below or above unity representing under- or over-cosine distributions, respectively. Returning to FIG. 20A, suppose that a normally incident ion beam removes $N_S$ substrate atoms per unit area or, equivalently, $N_S r dr d\phi$ atoms from some representative differential substrate element P. At some distance d away from P, that substrate element yields an atom fluence per unit area of $n_s(d) \cdot \cos^m \theta$ with proportionality coefficient $n_s(d)=(m+1) N_S \rho \delta \rho \delta \phi / (2\pi \delta^2)$, determined by normalizing the integrated fluence through a hemispherical surface of radius d, centered on P, to the number of atoms emitted. Including the projection factor cos φ sin θ to account for the angle between the atom fluence and the cylinder surface normal, the number of atoms striking the cylinder per unit area at some representative point Q is then $z^m \cdot (m+1) \cdot N_S \cdot \cos \phi \cdot r^2 dr d\phi / (2\pi (r^2+z^2)^{(3+m)/2})$, where cos θ, sin θ and distance PQ, are expressed in terms of r and z. Integrating over that half of the substrate visible from point Q then gives the total number of atoms $N_C$, hitting the cylinder per unit area at height o<z<L as:

$$N_C(z) = N_S \frac{z^m(m+1)}{\pi} \int_0^R \frac{r^2}{(r^2+z^2)^{(m+3)/2}} dr. \quad (2)$$

where R measures the effective substrate target size. In the limit R→∞, physically approximated by R>>L, for all m >o, $N_C$ reduces to $N_S \Gamma(m/2)/(2\pi^{1/2} \Gamma(m+1)/2))$ where Γ represents the gamma function. That is, $N_C$ becomes independent of height, implying uniformly thick wall coatings. Moreover, thanks to the sputtering anisotropy, approximately uniform coatings result already for R only a few times larger than L. As examples, a cosine distribution gives $N_C(z)=(N_S/\pi) \cdot [\arctan(R/z)-(R/z+z/R)^{-1}]$, implying a shell coating that, over the full cylinder length, deviates from its average thickness by no more than ±10 percent once R/L exceeds about 7. Meanwhile, for a $\cos^2\theta$ distribution, $N_C(z)=(N_S/\pi) \cdot (1+(z/R)^2)^{-3/2}$, implying similar wall-thickness uniformity already for R/L≥3. The sputtering anisotropy therefore facilitates efficient, parallel processing by allowing relatively closely packed arrays of structures on the processing substrate. Note, however, that as R/L shrinks further, maintaining wall-thickness uniformity requires ever more peaked sputter distributions and ever higher ion beam energies. Not needing excessively high beam voltages renders externally coated arrays of cylindrical posts preferable to internally coated arrays of cylindrical holes; while such an inverse approach can produce ring-like structures (Hobbs, K. L.; Larson, P. R.; Lian, G. D.; Keay, J. C.; Johnson, M. B. *Nano Lett.* 2004, 4, 167), the limited sputter target area implies low effective R/L values and substantial wall thickness variation for all but very short cylinders. Indeed the familiar redeposition of material ion-milled from within narrow channels, generally regarded as a deleterious, rather than as an exploitable, effect in microelectronics processing, is a geometrically similar problem with known non-uniform deposit thickness (Moreno-Marin, J. C.; Valles-Abarca, J. A.; Gras-Marti, A. *J. Vac. Sci. Technol. B* 1986, 4, 322).

Returning to cylindrical posts, FIG. 20B shows example wall thickness variations based on equation (2) for various sputter distributions. Equation (2) also quantifies the absolute wall thickness. For example, simplifying for R>>L, a cosine distribution (m=1) gives $N_C/N_S=\frac{1}{2}$. Assuming unit sticking probability, the shell wall thickness is therefore one half the thickness of the original layer ion-milled off the substrate. In this way, the nanometer-level height control common to planar thin-film layers translates into similar nanometer-level width control of thin, vertically oriented surfaces. Since the above analysis is not necessarily particular to a cylinder, it should be possible to similarly fabricate various other high-aspect-ratio structures; a caveat is that some alternative structure geometries may limit substrate visibility, implying locally differing limits to, and possible couplings between, the above R- and φ-integrals. Note also that equation (2) is strictly valid only for thin coatings (t<<L); for thicker coatings, the possibility of appreciable time-dependent modification to surface normals as substantial sidewall material accumulates, as well as the possibility of ion erosion of, and reflection from, that accumulated material cannot be ignored. While negligible for the high L/t aspect ratio thin-walled structures described here, general theory behind such secondary effects can be found elsewhere (Moreno-Marin, J. C.; Valles-Abarca, J. A.; Gras-Marti, A. J. *Vac. Sci. Technol. B* 1986, 4, 322; Smith, R.; Tagg, M. A.; Walls, J. M. *Vacuum* 1984, 34, 175).

FIGS. 21a-21f provide a schematic illustration of a fabrication process according to an embodiment of the current invention. Atop a sacrificial gold layer, cylindrical posts of radius ρ are patterned out of a photoresist layer of thickness L (FIG. 21a). To avoid resist exposure to the ion beam, and to aid structure release (described below), a thin sacrificial copper layer is evaporated obliquely (FIG. 21b), coating the substrate everywhere except within the shadows cast by the cylindrical posts. This is followed by evaporation of the desired magnetic material (FIG. 21c) and its subsequent removal from the substrate and the tops of the posts via argon ion beam milling (FIG. 21d) that leaves behind the redeposited sidewall coatings detailed above. A selective wet-etch of the underlying protective copper followed by an acetone resist removal then leaves the desired hollow cylinders (FIG. 21e), each attached to the substrate around just one half of their base, corresponding to their shadowed sides that did not receive any copper coating previously. This keeps the hollow cylinders still attached to the substrate for further processing, if desired; meanwhile, with the cylinder-substrate connections thus pre-weakened, the shells can also be removed via either a gentle ultrasound or a selective wet-etch of the underlying sacrificial layer (FIG. 21f). Note that the copper layer is not essential but including it does ease the resist removal and provide the option of a subsequent water-based ultrasound release free of any metal etchants or solvents.

For the case of cylindrical posts the magnetic material evaporation could also be performed at an oblique angle (as per the copper evaporation) provided that the substrate was continually rotated throughout the evaporation. However, while oblique evaporation can coat the post sidewalls, it will also coat the substrate which will therefore still require subsequent ion-milling and be subject to similar sidewall redeposition. Only for evaporation at grazing angles to the substrate would the more complex rotated evaporation be advantageous, but then the shadowing resulting from such high angles would limit the general applicability of the technique and the spatial density of structures that could be patterned. Note also that although coating the substrate could be avoided by instead obliquely shadow-evaporating (Dickey, M. D.; Weiss, E. A.; Smythe, E. J.; Chiechi, R. C.; Capasso, F.; Whitesides, G. M. *ACS Nano* 2008, 2, 800) or sputtering (Wang, S.; Yu, G. J.; Gong, J. L.; Li, Q. T.; Xu, H. J.; Zhu, D. Z.; Zhu Z. Y. *Nanotechnology* 2006, 17, 1594) onto an inversely patterned array of cylindrical holes rather than posts, such geometries preclude uniformly thick wall coatings. Because of the circular cross-sections, line-of-sight penetration depths of evaporant material vary across each hole, resulting in cylindrical shells whose wall thicknesses taper down from top to bottom.

FIG. 22A shows a scanning electron micrograph (SEM) of a sample array of fabricated nickel nanoshells that have undergone a partial wet-etch release. The shells have wall thicknesses, t≈75 nm, radii ρ≈µm, and close-to-optimal cylinder aspect ratio's L/2ρ≈1.2, implying wall height-to-thickness aspect ratios L/t, of around 30. Despite their thin walls, the cylindrical shells yield physically robust, self-supporting structures that are undamaged during either wet-etch (FIG. 22A) or ultrasound release (FIG. 22B). Forgoing any wet-etch, nanoshells were ultrasounded off their substrate into a vial of water and then pipetted out onto fresh substrates both in the absence, and in the presence, of an applied background magnetic field. Because of their high L/t aspect ratios, the structures' magnetic shape anisotropies ensure the necessary automatic alignment with the applied field direction (FIG. 22B).

FIGS. 23A-23D show experimental z-spectra (Grad, J.; Bryant, R. G. *J. Magn. Reson.* 1990, 90, 1) acquired on an 11.7 T MRI scanner from four different arrays of cylindrical nanoshells submerged in water. Each frequency point in the z-spectra was acquired by first applying a train of off-resonant π/2 pulses to saturate out the magnetization of protons with matching off-resonance precession frequencies, before an on-resonance pulse was used to excite and quantify the amount of remaining unshifted water. Showing the frequency-dependent saturated proton magnetization $M_S$, as a fraction of the total proton magnetization $M_0$, the spectra record the magnetic fields to which the water molecules were exposed. In particular, the spectral peaks (appearing as absorption dips in the curves) measure the fraction of water that diffused through the cylindrical nanoshells' internal homogeneously shifted magnetic field regions. All nanoshells used had $J_s$≈0.6 T (nickel), structure aspect ratios L/2ρ≈1.2, and inter-particle array lattice spacings of 3-4 times the particle diameters, but to test the theory presented here they were fabricated with different overall sizes, wall thicknesses, and incident $Ar^+$ energies. The spectra in FIGS. 23A and 23B are both from ρ≈1 µm cylindrical shells, both sputtered at incident ion energies of 300 eV, but with different wall thicknesses of t≈75 nm and t≈150 nm, respectively. By contrast, the spectra of FIGS. 23C and 23D are from ρ≈425-450 nm shells, sputtered at 500 eV, with t≈40 nm and t≈50 nm, respectively. All frequency shifts fall within about 10% of the predictions of equation (1), and the narrowing linewidths of those shells sputtered with higher energy ions suggest the improving wall thickness uniformity predicted by equation (2). Further increasing $Ar^+$ energy should further sharpen the resonances; meanwhile, the fact that these resonances are already easily resolved, speaks to the method's intrinsic high levels of uniformity in both sidewall thicknesses and overall structure geometries.

Although all demonstrated nanoshells were made from nickel, an advantage of their physical, rather than chemical, deposition is that most other materials amenable to vapor deposition could be readily substituted and that multi-layered shells could be similarly fabricated. For example, ion-milling a pre-evaporated tri-layer gold-nickel-gold or titanium-nickel-titanium film would transform those planar tri-layer films into hollow magnetic cylinders coated in gold or titanium. Depending on the application, such non-magnetic coatings could serve as oxidation barriers, offer further mechanical strengthening, or provide surface coatings that are biologically inert (titanium) or that facilitate common bioconjugation protocols (gold).

Being analogous to a superposition of rotated double-disk structures, the cylindrical shells naturally share many of those structures' advantages including large, continuously tunable spectral ranges that do not depend on $B_0$ for typical MRI scanners, and relatively low concentration requirements (Zabow, G.; Dodd, S.; Moreland, J.; Koretsky, A. *Nature* 2008, 453, 1058). Additionally, like their double-disk counterparts, the cylindrical shells can function as local physiological probes. For example, if the cylindrical shells were blocked by some substance designed to break down under certain physiological conditions then the shells could act as sensors with their spectral signals turned on or off depending on whether their internal regions were opened or closed to the surrounding water as suggested in FIG. 23E. A key difference between the cylindrical shells and the double-disk structures, however, is that with the disk spacing determined by separate posts, the double-disk resonances are potentially dynamically adjustable. On the other hand, the cylindrical shells' single-element construction is simpler and their synthesis more scalable in the nano-regime.

While the hollow cylinders' internal fields are relatively uniform, their external fields exhibit rapid spatial decays that manifest themselves as the frequency-broadened, but unshifted, background water signals seen in the experimental spectra of FIGS. 23A-23D. This broadening is due to the shortened $T_2^*$ due to the transverse magnetization dephasing caused by the particles' spatially varying external fields. Externally, therefore, the magnetic nanoshells function as $T_2^*$ contrast agents. This is shown in the MRI of FIG. 24 that shows darkened spots, typical of the $T_2^*$ contrast of regular superparamagnetic iron oxide (SPIO) nanoparticle contrast agents (Weissleder, R.; Elizondo, G.; Wittenberg, J.; Rabito, C. A.; Bengele, H. H.; Josephson, L. *Radiology* 1990, 175, 489; Wang, Y. X.; Hussain, S. M.; Krestin, G. P. *Eur. Radiol.* 2001, 11, 2319; Nelson, K. L.; Runge, V. M. *Top. Magn. Reson. Imag.* 1995, 7, 124), but that now identify the spatial locations of cylindrical nanoshells that have been suspended in an agarose imaging phantom. This SPIO-like contrast is not surprising since at typical MRI spatial resolutions, which exceed nanostructure sizes by orders of magnitude, a hollow shell and a solid particle present similar dipolar field profiles and contrast depends only on magnetic moment. With each cylindrical shell's material volume being equivalent to that of a solid sphere of diameter $(12L\rho t)^{1/3}$, comparison with similarly sized particulate agents (Shapiro, E. M.; Skrtic, S; Koretsky, A. P. *Magn. Reson. Med.* 2005, 53, 329) (that often contain only a small percentage of iron-oxide) suggests that contrast from individual nanoshells is easily resolvable and that many of the dark spots in FIG. 24 are due to individual shells. Said another way, the hollow cylinders therefore double as both spatial and spectral MRI agents with their dipolar far-fields providing spatial contrast while their tailored internal, or near-fields, provide spectral contrast.

In conclusion, this example demonstrates that controlled local redeposition of back-sputtered material can provide a simple route to large-area parallel fabrication of monodisperse, self-supporting nanoscale structures. The technique's patterning accuracy affords new applications such as, but not limited to, spectrally tunable MRI contrast agents that depend on precisely dimensioned resonance-shifting cylindrical magnetic nanoshells. Simultaneously providing also $T_2^*$ contrast, these multi-spectral nanoshell agents can provide an appealing complement to existing nanoparticle-based MRI agents, for example.

Example 3

FIG. 25 is a schematic illustration of a magnetic resonance structure according to another embodiment of the current invention. In this case, a thin ring-like magnetizable structure (shown in wire-frame view, but intended to represent a solid ring of material) surrounds or is attached to the inside walls of a stent, for example. The ring could also be replaced with a pair of two magnetizable elements on opposite sides of the stent (FIG. 26) or with multiple pairs of magnetizable elements at the same longitudinal position along the stent but rotated around the stent axis by different angles, where each pair consists of one piece on each opposite side of the stent. In other embodiments, there can be so many pairs arrayed around at different angles that combined they effectively add up to approximately the ring structure again. The geometry that is more favorable may depend on the type of stent (i.e., whether it is intended to be expandable via a catheter balloon or not. The spectral shift from these attached magnetizable structures then allows blood flowing through the pair(s) of magnetizable elements (or ring) to be spin-labeled so that blood flow (both speed and, through frequency-shift-dependent stent diameter indications, mass-flow) can be measured. Such spin-labeling, alternatively also known as spin-tagging, can be performed by, for example, irradiating with resonant RF electromagnetic radiation to specifically spin-tag nuclear spins passing through the magnetizable structure (while fluid not flowing through would be unaffected since it would not be resonant with the RF irradiation). Also, if the artery should narrow, then the stent diameter would shrink, or if the stent itself was in some way damaged or started to collapse, the change in spacing between magnetizable elements would change the resonant frequency shift of the protons in the blood flowing between them, allowing non-invasive RF measurement of artery collapse or warning of possible imminent stent collapse. There can also be multiple magnetizable rings or pairs of magnetizable elements spaced at determined intervals longitudinally along the stent in some embodiments of the current invention, e.g. to provide redundancy, to be used for alternate blood flow speed measuring (perhaps via time-of-flight techniques), to increase signal etc. In addition the same scheme can be envisioned without any stent at all, but simply with the magnetic elements arrayed this time around the outside (instead of against the inside walls) of a vein/artery to monitor blood flow within that artery The stent concept of spin-tagging fluid as it passes through the uniform field region between the magnetic structures, or within the magnetic tube-like structure, is also extendable to various other fluid networks beyond simply those involved with blood flow. For example, applications could include measuring/imaging/detecting flow within a microfluidic channel or network as exist, for example, in various microchip based chemical and biological assays (sometimes to referred to as lab-on-a-chip systems). Further examples extend also to larger size scales and could include also industrial pipes/pipelines where the magnetic structures, suitable arrayed externally about the pipe, or contained within the pipe (for example, attached to the inner walls), could provide flow monitoring capabilities even if the pipes are non-transparent, including the abilities to observe where fluid subsequently flows, what speed it flows at, and how the flow speed varies across the pipe.

In the example that follows we demonstrate the concept of flow 'tagging' with a large cylindrical version of a magnetic resonance structure according to an embodiment of the current invention. Two tubes are wrapped with a layer of nickel one of 50 um thickness and the other 100 um thick.

Water is passed through the tubes, one at a velocity of ~1 m/s and the other at ~0.5 m/s, as shown in FIG. 27. As water passes through the magnetic cylinder it is labeled with an RF pulse at the Larmor frequency inside the structure. This leads to a drop in the signal when an image is taken at some time after when the labeled water has moved to the imaging region.

This is shown clearly in FIG. 28, for the left tube with the slower velocity. The characteristic parabolic laminar flow profile can be seen in the three tags. A similar result is seen in FIG. 29 with the faster velocity. The frequency separation of the tags is evident in that labeling of one tube does not affect the other tube, so that each channel may be tagged separately.

Such an process may also be applied to perfusion imaging where the RF labeling pulses are spaced close enough in time so as to appear continuous in an image, as shown in FIGS. 30 and 31 for the left and right tubes, respectively, where in this case half of each tube is darkened.

Some embodiments of the current invention include "top-down" methods of producing magnetic resonance structures. Other embodiments of the current invention include "bottom-up" methods of production, such as chemical synthesis, of magnetic resonance structures. The requirements of generating uniform fields impose stringent conditions on the structure geometry (i.e., structures must be specific exact shapes). Moreover, in the case where an ensemble of structures are used, the level of inter-particle variability should ideally be minimized to ensure that there is no substantial broadening of the overall spectral signal from that ensemble. These two requirements strongly favor a top-down approach over chemical synthesis methods, since chemical synthesis generally cannot match top-down's level of precision in structure shape definition and inter-structure monodispersity.

However, in certain situations, for example, where only a few distinct spectral shifts are required at any one time, it may be possible to sacrifice some fabrication precision (and hence, spectral distinctness of the resulting agents). In such situations certain well-controlled chemical syntheses may have a high enough degree of control and monodispersity to provide practical fabrication methods.

In addition, it may also be desirable to chemically synthesize a large batch of structures and to then perform a separation and/or filtering step to select out only those structures from the large batch that have the right geometrical shapes to fall within a suitably narrow band of sizes and shapes. Although typically highly wasteful, the often much higher throughput of chemical synthesis versus top-down fabrication, may still render this approach attractive in the end for some applications. In particular, with the structures being magnetic, one could imagine a filtering/separation step that filtered out the desired structures based on the structure magnetic moment. For example, with the batch of structures suspended in some fluid, one can use an external magnet field gradient to create a force on the structures that drags them through the fluid. In such a case the speed of the particles moving through the fluid would be determined by a balance between Stokes drag of the fluid and the translational magnetic force, and hence would depend, among others, on the particle shapes and magnetic moments. Therefore, after flowing under the influence of the applied magnetic field gradient, the differently sized/shaped/composed structures would tend to spatially separate out within the liquid stream and a certain group could be specifically selected from that stream based on their location within it. The members of this particular group, just a small fraction of the whole batch fabricated, may then exhibit a high degree of monodispersity and may each have the right shapes.

Examples of specific chemical synthesis routes, can include the following:

i) They could be formed using a template structure such as a porous membrane substrate that might be formed from, for example, anodic alumina. For example, filling the cylindrical pores within an anodic alumina structure with one material, then chemically processing the structure to enlarge pore sizes, and then filling in the subsequently opened annular ring with another material (this time, magnetic) would leave hollow cylindrical structures once the inner material and the anodic alumina template have been selectively chemically removed.

ii) One could start with an ensemble of solid cylindrical rods suspended in a solution, (for example, gold nanorods are a commercially available product) and then via, for example, electroless plating, or galvanic deposition, coat such rods with a layer of magnetic material. Here however, it would be important to first have a method to selectively chemically passivate the ends of the rods, such that plating occurred only around the sides. Selectively etching out the central rods would leave only the plated cylindrical shell. Again, with the starting cylindrical rods generally exhibiting considerable variation in diameter/length, a filtering/separation step would be performed to select out just those hollow cylinders that are of the right shapes.

The magnetic resonance structures were described in reference to some examples according to particular embodiments of the current invention. The general concepts of the current invention are not limited to only these specific examples. The exact geometry of the microstructure, the number and relative arrangements of magnetic portions, the composition of possible non-magnetic fillers, and the composition of the magnetic portions can be designed for specific applications. For example, other applications may include, but are not limited to, the following:

Standard reference frequency shifts for MRI calibration/testing/fabrication.
  These may include, for example, a fixed set of microstructures, where each member of the set has a different spectral shift, thus enabling one to calibrate MRI and/or NMR equipment in terms of absolute and relative frequencies.

MRI spatial calibration markers/locators (when affixed to substrate)
  Here for example, a set of microstructures might be arrayed in some regular/geometrically prescribed arrangement with known spacings/angles between various microstructures, firmly attached to a rigid substrate to provide a spatial calibration of measured distances and angles in an MRI machine Specific detection/labeling/tracking of biological cells
  Here for example, individual (or possibly some small number of) microstructures would be bound to/incorporated within certain biological cells. The microstructures might include specific biochemical coatings ensuring that specific microstructures specifically bind to specific cell types. This would enable tracking of cells and in particular, the ability to differentiate between different cell types by exploiting the different frequency shifts of the attached microstructures MRI fluid flow blood perfusion label
  Here for example, fluid flowing through the space between the microstructures' magnetic portions could be specifically spin-tagged by irradiating it with resonant RF electromagnetic radiation much as in the stent or pipe application described above. Here, however, the fluid may subsequently flow into some other region and, possibly, mix with other fluid already there. For example, this technique can show where fresh blood enters the brain and perfuses.

Magnetic field sensors

Because the resonance frequency of the microstructures determines an offset in the Larmor precession frequency of the nuclear magnetic moments that pass through the structure, the exact absolute resonant Larmor precession frequency of those magnetic moments would give a measure of the total field (=offset field due to structure+external fields). Alternatively, a geometrical array of structures could be set up, with each structure's geometry varied such that each structure's resonant frequency is purposely shifted by a determined amount from that of its neighbor(s). In this way a magnetic resonance image of the array would show a higher/lower signal at a specific location in the array (which was at resonance due to the shifting effects of an external field that one is trying to measure) and effectively transform the field measurement activity into one of locating the spatial position of this higher/lower signal.

Distance/pressure/vibration/torque sensors (all will affect the particles measurable frequency shifts through change in particle geometry)

Because the resonant frequencies of the nuclear magnetic moments within the space between the magnetic portions of these structures depends on the spacing between those magnetic portions, they may be able to measure a variety of physical phenomena by transducing that phenomena into a distance change between the magnetic portions.

Torque or orientational measurements.

Because the homogeneous field produced between the magnetic portions relies on the direction of magnetization of those portions, if the structure were reoriented with respect to an external magnetizing field, or if the magnetic portions were reoriented with respect to each other, this would modify the magnetic resonance signals received, giving an indication of some torque force(s) on the objects or simply a different angular orientation of the objects. For example, this may translate into a measurement of fluid flow pressures in the blood stream, where the alignment of the structure with respect to the MRI magnetic field would be determined by a competition between the magnetic self-alignment of the structures to the MRI magnetic field and the rotation/shear forces exerted by the flowing fluid.

Magnetic separation

Being magnetic, these microstructures could be used in the same manner as regular magnetic beads in traditional magnetic separation protocols.

As rotators of objects attached to them/magnetically driven rotary pump-like motion/fluid pump/mixer Because of the inherent magnetic shape anisotropy of many possible embodiments of the current invention, the inherent self-aligning force between the structures and an external field could be exploited to make fluid micropumps and micromixers, by rotating an external field and having the structure magnetically follow that rotation. Such rotation may also be useful for destroying, for example, cancerous cells by placing these microstructures within such cells and then rotating the external field to effectively churn up the cell's contents. If specifically coated to specifically bind only to cancerous cells, normal cells would effectively be unharmed.

Localized RF magnetic heating elements/targeted thermal ablation

Depending on the exact material composition of the magnetic portions comprising these microstructures, application of an alternating magnetic field that repeatedly magnetizes and demagnetizes the objects could be used to generate local heating for targeted thermal ablation/destruction of, for example, undesirable cell types.

Localized magnetic field gradients

In contradistinction to the homogenous fields in the space between the magnetic portions of these microstructures, the external fields of these microstructures afford high gradients that may be useful for alternate magnetic imaging techniques, or for generating highly localized high magnetic forces.

Micro-RFID tags

In this application the structures might be affixed to some other object allowing that object to be magnetically probed/recognized. Using microstructures with different frequency shifts allows distinction between different objects in much the same way as regular RFID chips do, except that here the signal is based on a magnetic resonance measurement. In this application the microstructures and the objects that they label may reside with a fluid/gas/gel suitable for magnetic resonance probing, or the microstructure might be packaged in a container with some amount of fluid/gas/gel surrounding it, and then that entire container would itself be affixed to the object to be RFID-tagged (in other words, the RFID-tagged object need not itself be within the liquid or gel).

RFID-enabled microfluidics

Here the microstructures would be used to tag/label objects flowing in a microfluidic stream, so that an RF readout of those objects transported in the stream can be made. This has advantages over traditional microfluidics because no optical line-of-sight is required. Apart from tracking objects moving in the stream, it could also be used to infer information about the fluid stream itself, such as its speed etc, by noting how the microstructures move within that stream. Because no optical line-of-sight is required, this may be useful for monitoring fluid flows in places that are awkward to access Flow cytometry This refers to that specific microfluidics application where objects passing by in the stream are tracked and counted and should be obvious from the above MD-enabled microfluidics discussion.

Flow sensors for stents

The invention has been described in detail with respect to various embodiments, and it will now be apparent from the foregoing to those skilled in the art that changes and modifications may be made without departing from the invention in its broader aspects, and the invention, therefore, as defined in the claims is intended to cover all such changes and modifications as fall within the true concept of the invention.

We claim:

1. A method of performing magnetic resonance imaging, comprising:

providing a plurality of magnetic contrast structures dispersed in a medium, illuminating the contrast structures with a source of electromagnetic radiation to excite the contrast structures with excitation radiation, and detecting characteristic magnetic resonance signals resulting from the contrast structures with a detection system, wherein said each contrast structure consists of a continuous shell of a magnetic material arranged as a substantially spherical shell or a substantially ellipsoidal shell, each contrast structure having one access hole and defining a hollow region therein, wherein the hollow region in the contrast structure creates a spatially extended region contained within a near-field region of the contrast structure over which the contrast structure on its own, or in conjunction with an applied magnetic field, results in a substantially homogeneous field, such that nuclear magnetic moments of a second material when arranged within said spatially extended region precess at a characteristic Larmor frequency, whereby the contrast structure, combined with the second material, is adapted to induce a characteristic magnetic resonance signal of the magnetic material.

2. The method of claim 1, wherein the magnetic material is arranged as the substantially spherical shell.

3. The method of claim 1, wherein the magnetic material is arranged as the substantially ellipsoidal shell.

4. The method of claim 1, wherein the contrast structure has a maximum dimension of less than about 5 cm.

5. The method of claim 1, wherein the contrast structure has a maximum dimension of at least about 10 nm and less than about 100 μm.

6. The method of claim 1, wherein the contrast structure has a maximum dimension of at least about 50 nm and less than about 10 μm.

7. The method of claim 1, wherein the medium is a liquid or gel.

8. The method of claim 7, wherein the medium is a liquid.

9. The method of claim 1, wherein said contrast structure provides a frequency-shifted nuclear magnetic resonance signal when used with at least one of a magnetic resonance imaging system or a nuclear magnetic resonance system.

10. The method of claim 8, wherein the contrast structure permits a fluid to at least one of flow through and diffuse through at least a portion of the spatially extended region of a local magnetic field created by the contrast structure.

* * * * *